(12) United States Patent
Haar et al.

(10) Patent No.: US 6,258,063 B1
(45) Date of Patent: Jul. 10, 2001

(54) HYPODERMIC INJECTION SYSTEM

(75) Inventors: Hans-Peter Haar, Wiesloch; Manfred Beuttenmüller, Ladenburg; Markus Mattern, Heppenheim, all of (DE); George Bevan Meacham, Shaker Heights, OH (US)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/341,766

(22) PCT Filed: Jan. 16, 1998

(86) PCT No.: PCT/EP98/00221
§ 371 Date: Sep. 24, 1999
§ 102(e) Date: Sep. 24, 1999

(87) PCT Pub. No.: WO98/31409
PCT Pub. Date: Jul. 23, 1998

(30) Foreign Application Priority Data

Jan. 17, 1997 (DE) ................................. 197 01 494

(51) Int. Cl.⁷ .................................................. A61M 37/00
(52) U.S. Cl. .......................... 604/141; 604/121; 604/132; 604/142; 604/185; 604/187; 604/212; 604/69; 222/92; 222/95; 222/633
(58) Field of Search ...................... 604/140, 118, 604/121, 122, 125, 131, 132, 141, 142, 145, 187, 181, 185, 212, 217, 204, 200, 244, 68, 69, 70, 72; 222/92, 93, 95, 633, 380, 207, 214, 389, 397, 399

(56) References Cited

U.S. PATENT DOCUMENTS

| 3,308,818 | 3/1967 | Rutkowski . |
| 3,381,403 | 5/1968 | Murdoch . |
| 3,387,609 | 6/1968 | Shields . |
| 4,059,107 | 11/1977 | Iriguchi et al. . |
| 4,955,871 | 9/1990 | Thomas . |
| 5,167,631 | * 12/1992 | Thompson et al. .................. 604/132 |
| 5,306,257 | * 4/1994 | Zdeb .................................... 604/131 |
| 5,318,540 | * 6/1994 | Athayde et al. ...................... 604/141 |
| 5,370,626 | * 12/1994 | Farris .................................. 604/187 |
| 5,538,506 | * 7/1996 | Farris et al. ......................... 604/187 |
| 5,571,261 | * 11/1996 | Sancoff et al. ..................... 222/386.5 |
| 5,871,125 | * 2/1999 | Gross .................................. 222/207 |
| 6,063,058 | * 5/2000 | Sakamoto ............................ 604/132 |

FOREIGN PATENT DOCUMENTS

| 3706532 C1 | 9/1996 | (DE) . |
| 749759A | 12/1996 | (EP) . |
| 1121237 | 7/1956 | (FR) . |
| 2026794 | 1/1989 | (GB) . |
| WO 94/24263 | 10/1997 | (WO) . |

OTHER PUBLICATIONS

Abstract for DE 3706532.
Abstract for EP 749759.

* cited by examiner

Primary Examiner—Richard K. Seidel
Assistant Examiner—Cris Rodriguez
(74) Attorney, Agent, or Firm—George W. Johnston; William H. Epstein; John P. Parise

(57) ABSTRACT

A hypodermic injection system allows for the generation of a high pressure liquid jet capable of passing through the skin. The system uses two regions, the first region being flexible or squeezable and the second region having at least one exiting orifice through which the liquid jet can be expelled. The flexible region can be deformed by a pressure change in the surrounding container generated by an activatable gas generator that generates pressure within the first region that causes the liquid to be expelled.

35 Claims, 11 Drawing Sheets

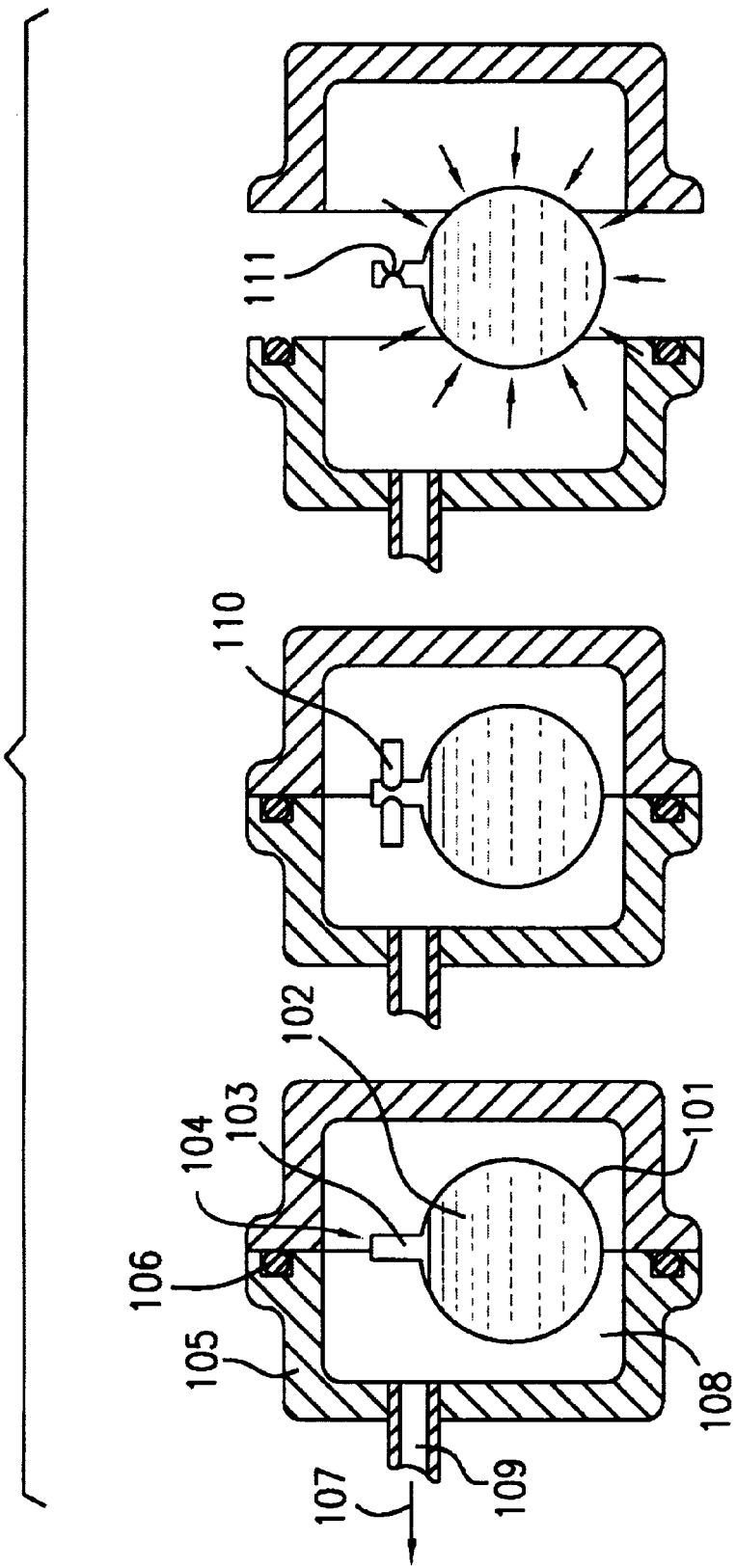

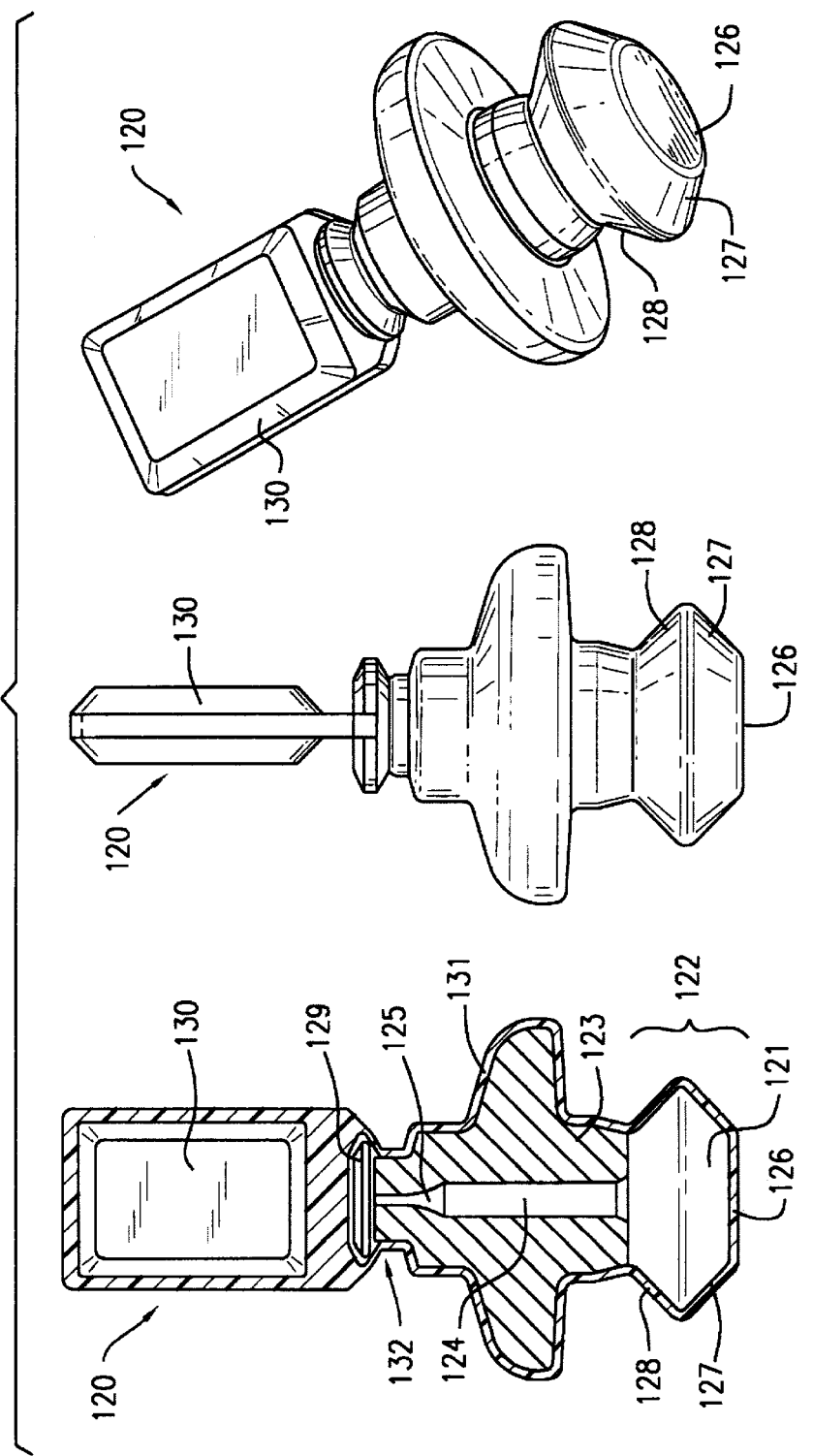

Figure 1:
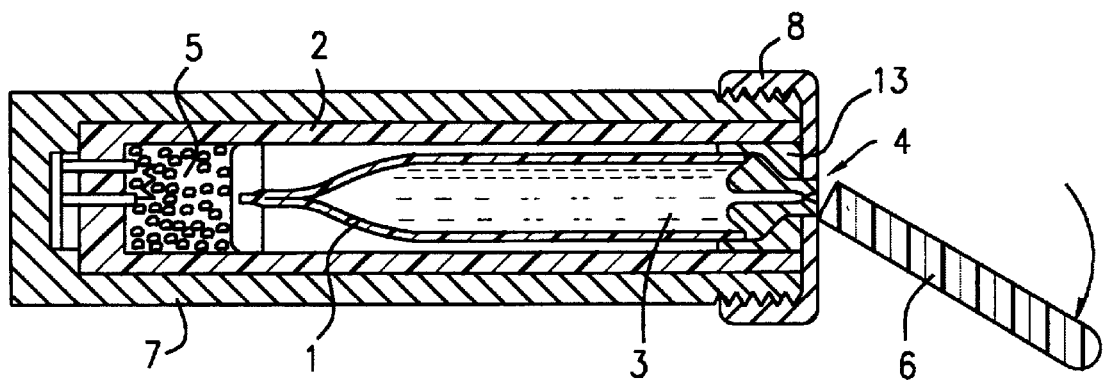

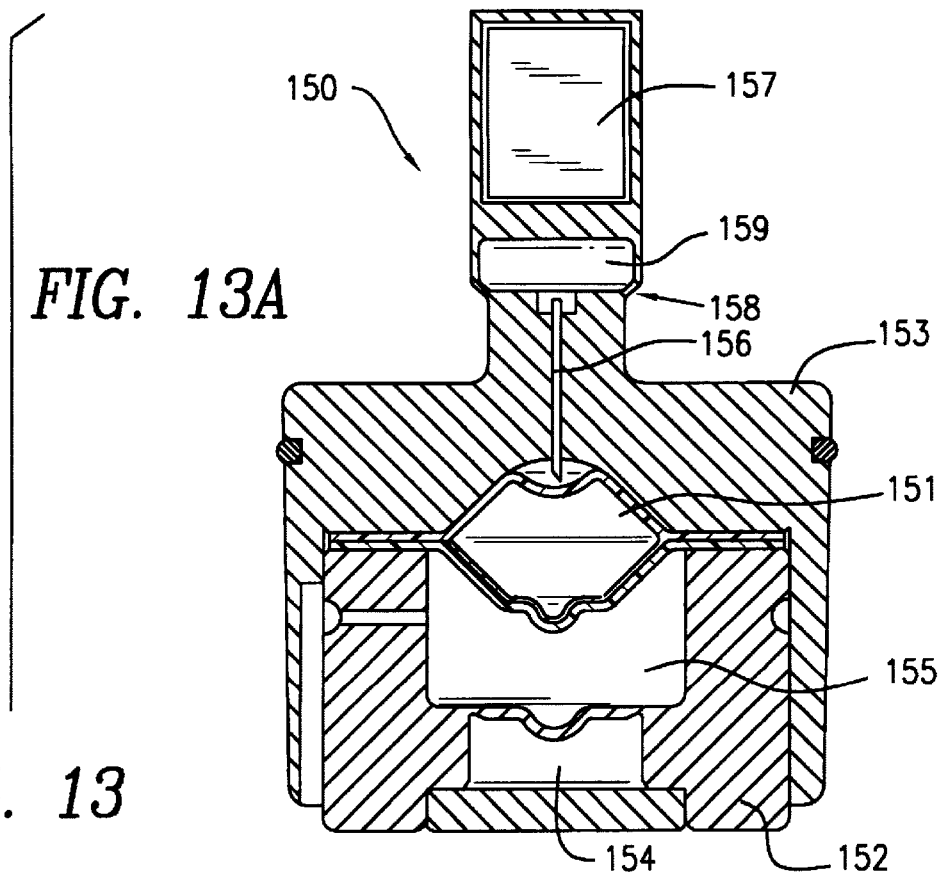
*FIG. 13A*
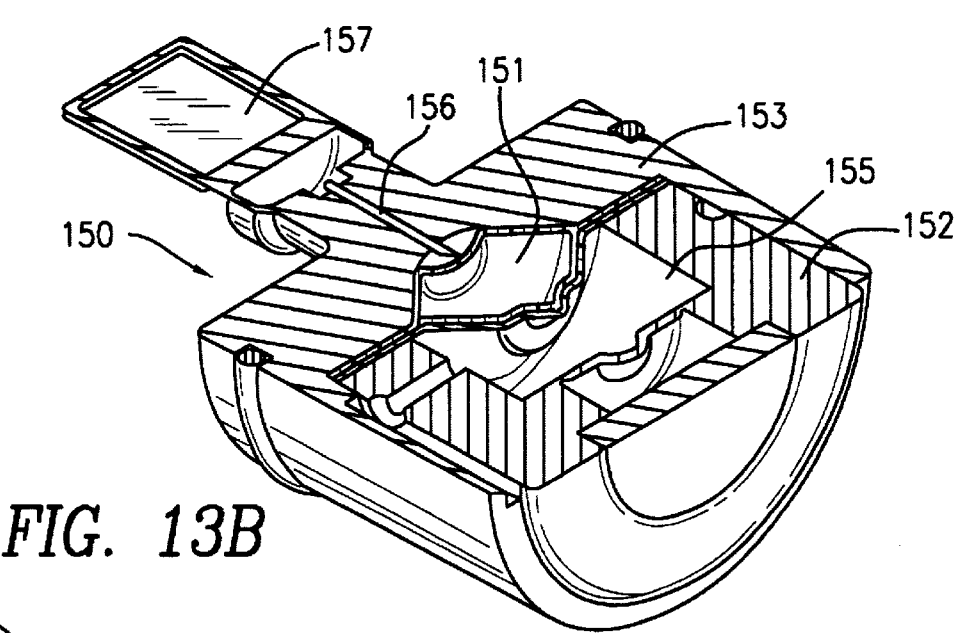
*FIG. 13B*
*FIG. 13*

HYPODERMIC INJECTION SYSTEM

This invention is in the field of the injection of liquid into tissue by generating a high pressure jet capable of passing through the skin.

Hypodermic injection system for fluids, comprising
a medication unit in which the liquid to be injected is stored and which has a first and a second region, said first region being squeezable or flexible and said second region having at least one orifice.
an explosion chamber in which the medication unit is located at least partially and a pressure generated within said explosion chamber is deforming said first region of the medication unit,
an activatable gas generator located inside the explosion chamber which generates a pressure within the explosion chamber when activated,
an activation unit for activating said gas generator
wherein said explosion chamber has a gas port connected to a free volume chamber having a variable volume.

A further aspect of the present invention are medication units which assure that the liquid medication does not contact insterile parts of the medication unit or the injection system prior to entering the skin.

In the field of medicine there are numerous methods for the targeted dispensing of medicines. Forms of medicine administration such as tablets, dragees, creams, and similar are all known. For a plurality of active ingredients such forms of administration are unsuitable because the physiologically active ingredient degrades before they can become active. In tablets which must be taken orally, the medicament, for example, has to be constructed such that it is resistant to aggressive stomach acids and on the other hand can be resorbed by the stomach or the intestinal wall into the blood circulation. For a large number of medicines it is not possible to develop a patient-friendly form of adminstration such as a tablet or a dragee. In such cases it is therefore necessary to introduce the medicine directly into body tissue or into the vascular blood system. Today it is usual practice that the injection occurs using a syringe. In the prior art however injection devices have been known for a long time which can be operated without using a hollow needle which is uncomfortable for the patient. Injection systems without a hollow needle employ a jet of liquid which is ejected at high velocity from an orifice and is capable of penetrating through skin and tissue. Such an injection is significantly less painful and can be performed by personnel who have not been trained in the use of syringes.

Injection systems employing a pressurized liquid jet of medication which penetrates the skin are called hypodermic injection systems within this application. Hypodermic injection is meant to include intra-dermal, subcutaneous and intra-muscular injections.

With an injection system in accordance with the invention, all medicines available in liquid form can be injected. The field of application covers for example painkillers (analgesics), insulin and also protein solutions. For protein solutions, especially solutions of human protein, remarkably it has been discovered that they can be administered substantially without any degradation by way of a high pressure jet.

Needle-free injection systems were described in the 50s and 60s. In U.S. Pat. Nos. 2,322,244 and 3,335,722 devices have been described, which use explosive substances for the generation of the necessary high pressure jet. Present-day systems, such as for example Vitajet® of the company Vitajet Corporation, employ a steel spring for the generation of the high pressure jet. A device which operates in an analogous manner is also marketed by Mediject Corporation. Such systems have the disadvantage that the user has to perform several awkward operational steps. First of all, the liquid to be injected is introduced into the injection device. Thereafter a steel spring is loaded by the rotation of device parts against each other. Especially for persons, who are ill or like many diabetics who are physically disabled, the necessary operational steps requires the application of enormous effort. An alternative to this system is offered by the aforementioned injection systems using explosives, because the energy from the explosive substance is used and a complicated loading of the spring is not necessary. The turning away from such systems which has taken place in the course of time is directly related to severe disadvantages with respect to hygiene and technical-safety aspects. U.S. Pat. No. 3,335,722 reveals, that cross-contamination of explosives and medicines are a particular problem of such constructions. In the U.S. patent an arrangement is suggested, in which capsules containing the medicine and the explosive substance are separated from each other and a special arrangement for the transfer of energy is employed. In the arrangement described an explosive is ignited by a contacting rod, as is the case, for example, with a rifle bullet. The gas resulting from the explosion accelerates a piston which is mechanically linked to a second piston which accelerates a rubber stopper which in turn forces a medicinal liquid out of the orifice on the opposite side. To prevent cross-contamination of combustion cases and medicine, complicated technical constructions are necessary which disadvantageously complicate the injection device and make it more expensive. Furthermore an ampule is required into which a rubber stopper is pushed. Because of the pressure in the ampule created by the movement of the stopper, it is necessary to make arrangements to ensure prevention of leaks between the ampule and the stopper. In this respect the choice of material for the ampule is critical, because a deformation when pressure is applied must not lead to leaks in the region of the stopper. The devices described in the prior art all exhibit generally the disadvantage that for the generation of pressure parts which can be compressed together, stoppers are employed and therefore sealing areas have to be controlled.

In the prior art there are also known devices for a needle-free injection of liquids which avoid stoppers or the like. European patent application 0 370 571 describes a system where an ampule which contains a liquid medication is being mechanically compressed by a rod. This compression drives the liquid medication through one or more orifices to generate a liquid jet. While this apparatus mostly avoids the problems associated with frictional surfaces and stoppers moving in a cylinder this apparatus has a drawback that the flexible part of the ampule may be destroyed when pressed by the rod. A further drawback of this device is that the pressures which can be applied to the ampule are limited due to the risk of destruction and also by the relatively low energy stored in a spring. Another disadvantage of this apparatus is that a mechanical compression of the ampule by a rod cannot guarantee that the liquid within the ampule is being ejected totally. Such a device is therefore insufficient when it is desired to inject a specific amount of medication.

In FR-1.121.237 there is described a device for the hypodermic injection of liquids using a high pressurized liquid jet. The device comprises a compressible container for liquid medication which is attached to a unit having a fluid channel. The unit with the fluid channel is connected to a unit with a nozzle so that a continuous channel is being formed through which the liquid medication can be expelled. For a hypodermic injection the unit with the channel is placed on a mounting element so that the medication container is surrounded by a chamber and pressure is applied to said chamber by ignition of an explosive. The apparatus described in FR-1.121.237 seems very similar to the present invention but has some technical drawbacks which are overcome by the present invention. The document FR-1.121.237 teaches that the medication container and the unit with the channel are combined by the user. The user fills the liquid to be injected into the medication container and tightly closes the medication container by screwing on the unit with the fluid channel. Such a process is not only cumbersome but it also bears the risk that the medication and/or the fluid channel is contaminated. The injection of a contaminated medical fluid is totally unacceptable in the therapeutic field. This problem of contamination is mostly unresolved in the prior art of hypodermic liquid injection. Furthermore the FR-1.121.237 does not give any information regarding the pressure of the liquid jet and how this pressure can be controlled to be in a specific range or how the pressure can be changed by the user to comply with his specific needs. A further drawback of the system described in FR-1.121.237 is that no means for purging air from the liquid chamber are described. However, air within the liquid chamber leads to disadvantageous effects as described further below.

Reference GB-697,643 describes a device for hypodermic injections using a flexible or collapsible element which is being compressed. The device described in this document is very complicated and uses a recheargable pressure chamber into which a pressurized gas is introduced and in addition thereto a chamber with a hydraulic fluid is employed. With this device it is possible to control the pressure by which the liquid is being expelled from the container. However, a flexible container is needed into which the collapsible medication container is being introduced. From the function of this device it must be assumed that it is impossible to expel all of the fluid which is within the medication container. The document GB-697,643 further discloses a medication container which is sealed and can be used to store a medication under sterile conditions. However, this document does not disclose a medication container including a sterile nozzle. Therefore this document does not give an overall solution to the object of sterile injection.

In the prior art there is also known a device for hypodermic injections as described in U.S. Pat. No. 3,308,818. A flexible medication container is being placed in a chamber and pressure is being applied to this chamber by an explosive to compress the medication container. While being compressed the medication container ruptures at the entrance of a fluid channel which ends in an orifice. The fluid is then expelled from said flexible containers through the fluid channel and is being injected into a human or an animal. This very simple device has a number of drawbacks compared to the present invention. The prior art reference U.S. Pat. No. 3,308,818 does not describe how to control the pressure generated by the explosive. Furthermore the device uses an area into which the wall of the flexible container ruptures when it is pressurized. The drawback of such an uncontrolled rupture is that small particles may be torn away from the flexible container which are introduced together with the liquid medication into the body. The injection of such particles may cause inflammations or allergic reactions. Another drawback of the system described in U.S. Pat. No. 3,308,818 is that the fluid channel and the nozzle through which the medication is expelled are not kept under sterile conditions. Injections with such a device therefore may lead to infections or inflammations.

Prior art in general discloses to pressurize a flexible medication container to expel a liquid jet which is able to penetrate the skin. However, even if this concept has been known for a long time no system is available on the market which uses this concept. This shows that there are still technical roadblocks which have to be overcome. The present invention discloses a system for hypodermic injections and medication units which overcome these roadblocks.

The object of the present invention was to provide an economically feasible but nevertheless reliable device for the needle-free injection of liquids. In particular, it was the object of the invention to exclude with certainty the cross-contamination of explosion gas and medicine by use of simple means. Furthermore, it was the object of the present invention to provide an injection device which can be operated by the user with a minimum of inconvenience and which is also of simple construction as well as economically feasible. This invention proposes injection systems and medication unit which avoid contamination of a liquid medication prior to penetration of the skin. A further problem which is solved by this invention is the control of the liquid jet pressure.

In the injection system of the present invention, frictional surfaces and sealing surfaces between moving parts of a medication container are avoided. Instead of these a medication unit is used which possesses a region which can be pressed together or is flexible and can therefore be deformed. This region envelopes the liquid medication to be ejected. The medication unit has also a second region with an orifice through which liquid medication can escape from the medication unit when the first region of the medication unit is deformed. The use of such a medication unit has the advantage that parts are avoided which have to be slid against each other, and sealing surfaces between these parts are avoided. To facilitate the squeezing or pressing together of the medication unit, the said container is located in a container which surrounds the squeezable region of the medication unit at least in part or borders the medication unit with its flexible region such that a pressure change in the container leads to a deformation of the flexible region. When pressure develops inside the container, similarly pressure develops in the medication container too whereby liquid is forced out of the orifice.

The first region of the medication unit is preferably made of materials which can easily be deformed, such as plastics or metal foils. For the generation of the effect in accordance with the invention, it is important that due to compression or by deformation no components are mechanically forced against each other such that frictional surfaces are caused, whose sealing is difficult to manage. The vessel shell in the first region remains closed during the pressing together of the components or deformation stage or the deformation which is possible due to the elasticity of the material in the first region. The deformation can result for example from the pressing together of a section of a wall whereby the elasticity of the wall material is used to ensure that the vessel shell remains closed. This, however, is associated with a relatively strong mechanical stressing of the wall which can be reduced in embodiments in which a compression of the wall material results or in which the wall traverses from a convex form to a concave form. In the last-named embodiment the surface of the first region in both forms is on the whole the same such that the severe expansion and contraction of the wall material is avoided.

In the embodiments described above, shearing and severe stretching of the wall material in the first region of the medication unit are virtually completely avoided. Therefore usually the wall material may have modest mechanical properties, since it must only withstand low stresses. Plastics such as polyethylene, polypropylene or PVC are for example suitable, whereby the wall thickness of less than a millimeter can be realized. Particularly suitable wall thicknesses are in the region of 100 to 600 $\mu$m. Metal foils having a thickness in the range named-above can also be employed.

The medication unit has a second region in which an orifice for the expulsion of liquid is located. For this purpose, an exiting channel is situated in the side of the second region which leads to the exiting orifice. The second region is furthermore mechanically stable to such an extent that no significant deformation occurs as a result of the pressure which develops in the first container. Aternatively, if the deformation is predictable, it can be allowed for in the design. A suitable geometrical arrangement should prevent the deformation of the exiting orifice. However, even such a deformation can be allowed for if considered in the design. A suitable diameter of the orifice is known to those skilled in the art from the prior art. When explosive substances are used, extremely high pressures can be generated such that smaller openings in the region of 80 to 130 $\mu$m are feasible. These openings of the exiting orifice are smaller than those of the prior art and the injection is less painful. There are no special requirements with respect to the geometrical form of the exit channel and the exit orifice. Advantageous is however a form in which the liquid jet is focussed. Particularly useful types of medication units including advantageous orifices are described further below.

For reasons of hygiene it is necessary to close the exit orifice to prevent liquid escaping and a contamination of the liquid in the first container. Preferably such a closure is realized by a knob/peg or the like which is connected to the second region by a predetermined breaking point. Furthermore, screw caps, lids and so on can serve this purpose.

The first and second region of the first container are advantageously formed as a single unit which, however, can comprise two or more pieces. The first container can in particular be fabricated as one unit, similar to the designs known for eye-drop ampules. First of all, the second region containing the exit channel is formed in an injection moulding process to which an open plastic jacket connects which later takes the form of the second region. Liquid is filled into the plastic jacket and the opening is sealed by welding the jacket material.

The system of the invention is advantageously constructed such that the act of squeezing together or deformation only occurs in the first region and no deformation of the second region occurs. Similarly the transition region from the first to the second region should also, as far as is possible, undergo little deformation.

In an advantageous embodiment, the squeezable first region of the medication unit is located entirely inside a surrounding container. It is furthermore favorable when the surrounding container is completely closed by the medication unit and possibly further material components such that no gas can escape even when there is higher pressure inside the system than in the surroundings. When the gas pressure builds up very rapidly, for example by the rapid combustion of an explosive substance, it is not necessarily required that the surrounding container is entirely closed to the surroundings. It is also possible to provide small openings through which gas can escape. When gas is generated very rapidly, the creation of pressure in the surrounding container is so rapid that during the explosion process no significant pressure drop takes place. In accord with the invention, a pressing or squeezing together of the first region of the medication unit occurs. Pressure inside the surrounding container drops only slowly as a result of the escape of gas. Such a embodiment of the injection system can be of advantage when the combustion gas contains mainly constituents which do not condense at room temperature because in such cases high pressure would remain in the second container after use of the injection system. This is normally not disadvantageous but can however lead to a deformation of the container in embodiments having a thin-walled second container which is disconcerting for the user. If gas generators, are used where the amount of substances which condense at room temperature is so large that after use of the system for injection, no significant excess of pressure remains in the surrounding container, then openings in the surrounding container are usually not necessary.

A further aspect of the present invention are medication units suitable for hypodermic injection. Such medication units have to comply with some specific needs:

They have to assure that the medication injected into the body does not come into contact with insterile parts of the medication unit or the injection system prior to entering the skin. Another requirement is to avoid substantial amounts of air or gas in the medication unit. It is expected that most of the air will escape between nozzle and skin during injection but air might be carried beneath the skin if the nozzle is tightly pressed against the skin surface. Additionally gas or air within the medication unit may cause interruptions in the jet stream and fluid motions perpendicular to the stream direction which can lead to incomplete injections or disadvantageous jet profiles. Furthermore the medication unit has to assure that the medication can be injected as completely as possible to control the amount of medication delivered to the user. It is a further requirement for the medication containers that they are made from a material that does not affect the medication even if the medication is stored for a time of months or years.

It has proven to be advantageous to employ medication units which are made from polyethylene, polypropylene or mixtures thereof since these materials do not affect the liquid medications we have tried. Since these materials have a low module of elasticity (they are soft) it is a further object of the present invention to provide nozzles which can withstand the pressure during the injection process. Prior art devices for jet injections employ nozzles made from hard plastics as polycarbonates, metals or ceramics.

It has shown to be of particular advantage to produce the medication units with the so called blow-fill-seal process. This process leads to medication units enclosing only very little gas. The blow-fill-seal process comprises generally the following steps:

a tube of softened plastic is closed at its lower end by compression, pressure is generated within the tube to press the softened plasic against the walls of a mold to form an open ended container, liquid medication is filled into the open ended container, the opening of the container is closed by compression and welding (e.g. with ultrasound or heated pinchers).

The before described process is well known in the art and for example described in more detail in "Plastic Mold Engineering Handbook" 4th ed., pp 540–545, Van Nostrand Reinhold, New York (1987) and DE 4439231.

Complete, bubble-free filling of containers produced by the standard blow-fill-seal process is not possible because the seal of the upper end of the container has to be made in a dry area to form a reliable weld. Therefore a headspace volume must be left empty. This results in an air bubble within the container. Within most applications such an air bubble is of no consequence as e.g. in case of eyedrop containers. However, air bubbles are unwanted within medication containers for hypodermic injections as explained before. The present invention therefore discloses new processes for the production of medication units for hypodermic injectors which avoid air bubbles in the medication unit.

A new-blow-fill-seal process which avoids gas within the medication units is described with reference to FIG. 11. This figure shows a vacuum approach to remove a headspace filled with gas. An open ended medication container (101) produced by conventional blow-fill-seal process was filled with medication (102). The container still has an opening (104) and a headspace (103) beneath. This medication container is placed in a chamber which can be evacuated. The chamber (105) shown in FIG. 11 has two halves and a seal (106) to form a gas tight sealing between these halves. When the chamber is closed a vacuum pump can be connected to the chamber by a channel (109) communicating with the interior of the chamber (see FIG. 11 A). Fortunately a hard vacuum is not needed to avoid a headspace. It has been shown that pressures of less than 0.025 atmospheres are sufficient to avoid bubbles.

After evacuation the medication container is closed by pinching the container opening as shown in FIG. 11 B. Advantageously the closing process can be performed by heated sealing tools (110) to form an air tight sealing (111). When the container is sealed and the vacuum in the chamber is released the chamber can be opened (FIG. 11 C). Atmospheric pressure acts on the container walls so that the headspace is filled with liquid.

Within this concept it has shown that some liquids tend to foam when a vacuum is applied due to gas physically absorbed in the liquid. Such a foaming is disadvantageous since liquid is pushed up and wets the closing area of the container. It is therefore advantageous to de-aerate the liquid by evacuation, warming up or other processes prior to filling them into the medication unit.

Within the present invention there is also contemplated to avoid the headspace by the following processes:

Prior to sealing the headspace of the medication unit is filled with carbon dioxide gas. After sealing the carbon dioxide is readily absorbed by the liquid.

The headspace is filled with gas of substances boiling between 35 and 85 degree celsius. After the sealing process these gases condense and the free headspace vanishes. Particularly useful substances are ethanol and ethyl-ether.

The headspace is filled with water steam which condenses after the sealing process The sealing process is made within an inert gas atmosphere as e.g. helium, methane or nitrogen. Preferred are small molecules which readily diffuse through the material of the medication container. After closing the container in the inert gas atmosphere the container is introduced into a vacuum to eliminate the gas from the headspace by diffusion.

The present invention is further directed to two concepts for medication units and handling units which are particularly suitable for hypodermic injections.

Injection system with adjustable injection pressure

An advantageous embodiment of the present invention is directed to a regulation of the liquid jet pressure. One measure to bring the pressure within the explosion chamber into a suitable range is to adapt the amount of explosive and the free volume of the chamber which surrounds the first squeezable container to each other. The chamber surrounding the first squeezable container will be called the explosion chamber in the following. The pressure created in the explosion chamber depends on the amount of gas which is generated by combustion of the explosive and the volume of the explosion chamber comprising the former volume of the explosive and the free volume surrounding the first squeezable container. The pressure applied to the first squeezable container further depends on the temperature of the combustion gas which depends on a number of variables as type of explosive, rate of explosion and so on. It has further shown to be advantageous to provide a gas port within the second container so that the combustion chamber communicates via this gas port with an adjustable free volume. By adjustment of this free volume the user can adjust the pressure of the liquid jet to his own specific needs. The adjustable free volume can be employed by a piston moving in a cylinder and means for fixing the piston at a specific position within said cylinder. This embodiment will be described in more detail with reference to a figure showing the free volume concept. Within the adjustable free volume concept it is preferred to employ a filter means which hinders particles of the gas generator from escaping the explosion chamber into the adjustable free volume. Furthermore, embodiments are claimed which comprise two free volumes which are connected to each other. At least one of these two volumes is adjustable.

An injection system of the invention consists of furthermore an activatable gas generator. Possible gas generators are for example explosive substances such as black powder, nitrocellulose, pentaerythrittetranitrate and the like. Of particular advantage are explosive substances which do not contain heavy metals such as lead or mercury, thereby avoiding environmental pollution because such substances nearly completely degrade to carbon dioxide, nitrogen and water upon explosion. Nitrocellulose, a propellant which is a preferred for the present invention produces substantial amounts of non-condensable gases, but no solid salt residues. Other propellants produce water vapour, which is condensable, and salt residues.

The explosion or kinetics of combustion can be controlled by selection of the explosive substance and its geometrical form. In the context of the present invention it is advantageous when the explosive substance does not combust in an explosive manner, i.e. the pressure wave generated by the combustion has a velocity less than the speed of sound. It is particularly favorable when the total combustion of the explosive substance lies in the time period of 10 to 20 msec. To achieve this, the explosive substance is usually highly compressed to slow down the progression of the zone of incandescence. A further factor which influences the kinetics of the increase in pressure is the size of the hollow in the second container, which prior to the activation of the gas generator is filled with gas or air. The larger the space for gas, the slower the build up of pressure.

Other devices can serve as gas generators which are suitable for the build up of pressure in the second container. Such a device can for example be a further container with extremely compressed gas or gas which was liquified under pressure (such as for example $CO_2$ in a pressure vessel). Compressed gas which can be filled on-site, such as for example is known in the case of $CO_2$ cartridges for siphons or the gas can be compressed by the user himself as is the case in commercially available hypodermic injection systems.

In the present invention a concept can be used where a spring is loaded by the user which forces against the pistons of a cylinder and compresses the gas in the cylinder. In this embodiment the second container of the system of the invention can be formed like a cylinder into which a piston enters powered by a spring. The pressure generation can be controlled by releasing the spring. In systems which operate using compressed gas filled on-site, the release can occur for example by the piercing of a seal in the pressurized container. Such a process is for example also used in $CO_2$-siphons in which a $CO_2$ canister is screwed onto a sharp hollow needle whereby in so doing a metal foil in the $CO_2$ canister is ruptured allowing the $CO_2$ gas to flow out through the hollow needle. However, $CO_2$-driven systems without pressure transformation are generally not suitable within the present invention. But there are known concepts to multiply the pressure e.g. with a large piston driven by $CO_2$ pressure which is connected to a small piston generating a higher pressure.

Furthermore the gas generation can result from the rapid evaporation of a liquid for example by use of an electrical heating spiral or by the electrical degradation (electrolysis) of a substance (usually a liquid) to a gas. An example of the latter process is the electrolysis of an aqueous solution yielding gaseous products, usually hydrogen and oxygen. Furthermore, chemical processes for the generation of gas can be employed, for example the reaction of fine aluminum with sodium hydroxide solution, thereby liberating hydrogen.

A hypodermic injection system possesses an exiting orifice, through which liquid from the medication unit can escape. Preferably, the exiting orifice which is part of the medication unit serves as a nozzle through which a liquid stream/jet can be injected directly through the skin. Embodiments are also possible in which the exiting orifice leads into a nozzle, through which liquid is ejected. This is for example possible when the medication unit and its second region in which the exiting orifice is located forces against a unit in which the nozzle is located such that exiting orifice and nozzle create a continuous channel. It is, however, preferred to employ medication containers which are directly in fluid communication with a nozzle. The injection of the liquid with the system of invention can occur via an exiting orifice or via a nozzle. The term nozzle implies simply that the channel through which the liquid exits the first container has a form which, by virtue of its geometry, can control the flow of liquid. Liquid penetration to deeper tissue layers may be achieved by focussing the jet, and the generation of a diffuse jet results in an injection reaching upper tissue layers. However, penetration depth can be controlled by the jet pressure and the orifice diameter. Larger jets penetrate deeper at a given pressure, since they remain coherent longer before bereaking up. It has been discovered to be of importance that the nozzle or the exiting orifice is positioned close to the surface of the skin. If the distance is too large, the momentum of the liquid decreases and the jet cannot penetrate the skin. Providing the liquid jet is focusssed by the nozzle or the exiting orifice, a distance of several millimeters between the skin surface and the exiting orifice can be tolerated.

In cases in which the liquid leads to undesirable irritation of the surrounding tissue at higher concentrations, two or more exiting orifices instead of only one orifice can be provided through which the liquid to be injected may pass. Such means achieve the distribution of liquid over a larger area of tissue and local concentrations can be kept at a lower level.

Devices known in the prior art which operate using a steel spring or a compressed gas have the disadvantage that the pressure which can be generated by such means is relatively low and as such nozzles have to be employed which have a diameter between 130 and 200 $\mu$m. In the preferred embodiment of the invention which makes use of explosive substances in contrast much higher pressures can be generated such that nozzles with a diameter of less than 130 $\mu$m may be employed for these purposes at hand. Nozzles or exiting orifices having a diameter of between 80 $\mu$m and 130 $\mu$m are favorable because very efficient injections using nozzles in this size range can be performed. Particular preferred are nozzle sizes in the range of 80 to 100 $\mu$m.

A particular advantage of this invention is that the system of injection can be fashioned in a very compact and user-friendly manner. This is on the one hand because of the fact that when using explosive substances as a gas generator the space required for the gas generator is very small and also the means for the activation of the gas generator can be of very simple design. Furthermore, it is possible using the system of invention to make disposable modules commercially available, which consist of a medication unit, a surrounding container (which provides an explosion chamber) as well as a gas generator located within the surrounding container. Such a disposable module has only to be inserted in a handling facility, which contains an activator for the gas generator. It is even possible to provide a disposable injection system which in addition comprises a device for the activation of a gas generator. Such a system can for example be realized using an explosive substance as a generator, whereby the explosive substance is made to explode by the action of a friction igniter. Advantageously, the activation of the gas generator can occur using a piezo igniter such as for example is known for fire lighters.

The advantage stated previously, namely the possibility of making disposable modules commercially available is particularly justified due to the fact that the gas generator can be integrated into the module whereas in systems described in the prior art the gas generator has to be integrated into the handling unit. Particularly suitable as gas generators for such a disposable module are those in which the energy is stored in a potential form and does not have to be generated by the user himself for example by virtue of his loading of a spring. Particularly preferred are explosive substances as gas generators.

The present invention additionally facilitates the possibility of providing systems which are composed of two or more components. In such systems the medication unit is inserted into a surrounding container and the arrangement is closed in such a manner that the gas generated in the surrounding container can not escape but rather exerts pressure on the squeezable region of the medication unit. In such an embodiment of the invention, a surrounding container usually is part of a handling unit and the handling unit possesses a device with which the arrangement from a surrounding container and medication unit can be connected with each other in such a manner that gas can not escape from the surrounding container in the course of the injection process. A surrounding container can consist of a hollow cylinder in such an embodiment of the invention, such that the front face (cross-cut end) is open and through which the medication unit can be introduced. The cylinder is provided with a closing device in the region of the open front face which is opened when the medication unit is employed and thereafter can be closed in such a manner that the medication unit is sealed preferably in the second region.

In such two-component embodiments of the injection system, several types of gas generators can be employed as described above. These are for example explosive capsules which are positioned in the surrounding container prior to the injection or gas generators can be employed which operate using cylinders which in turn are powered by a compressed spring.

The invention is illustrated in more detail by the following figures:

FIG. 1: Injection system prior to the activation of gas generator

Figure 2:
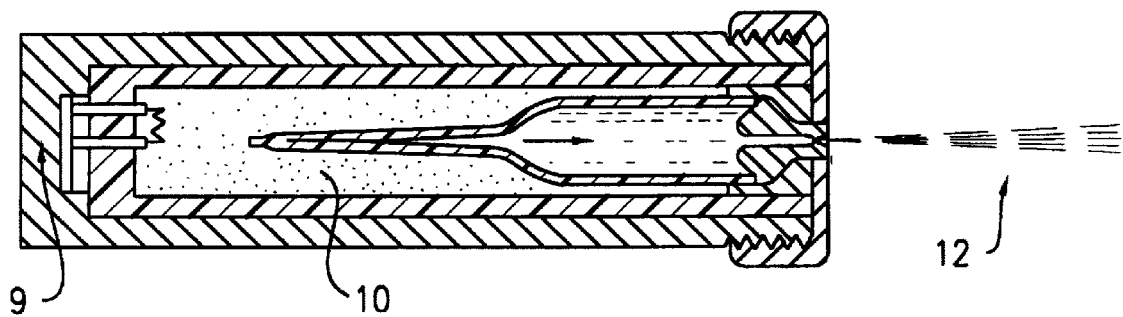

FIG. 2: Injection system after activation of the gas generator

Figure 3:
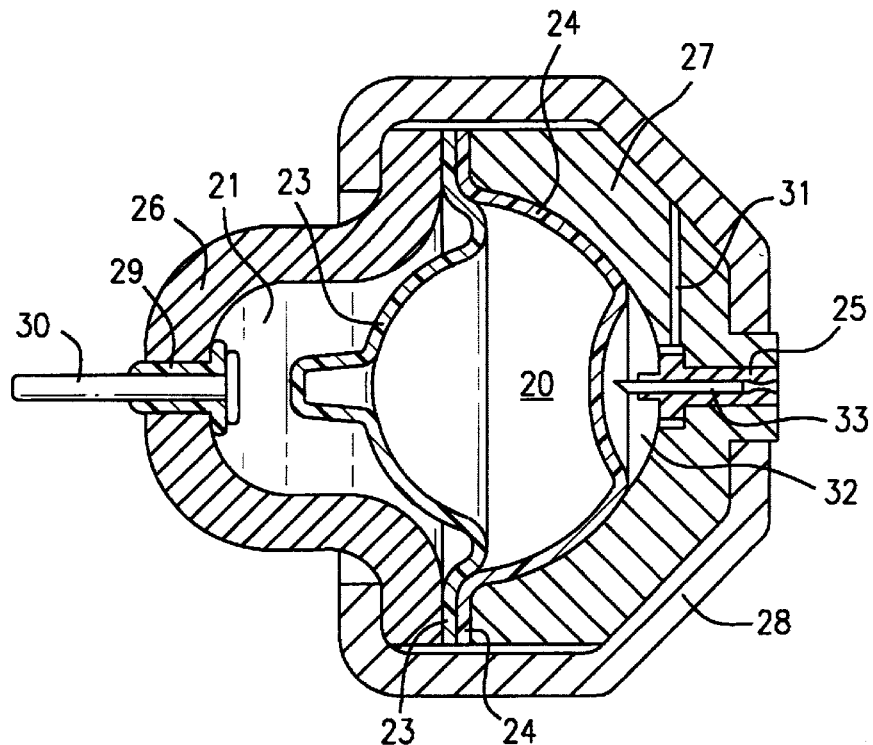

FIG. 3: Injection system with a medication unit having a membrane and a surrounding container (prior to injection procedure)

Figure 4:
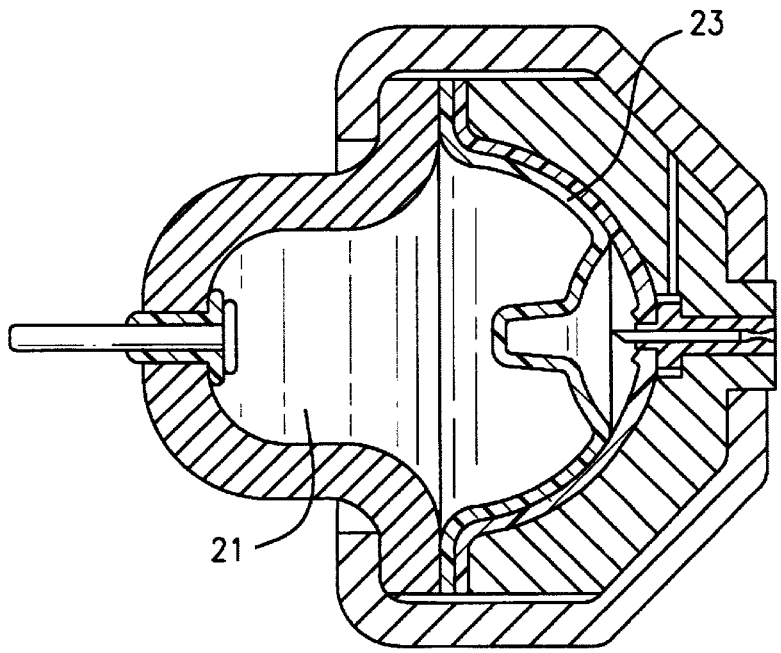

FIG. 4: As in FIG. 3 after the injection process

Figure 5:
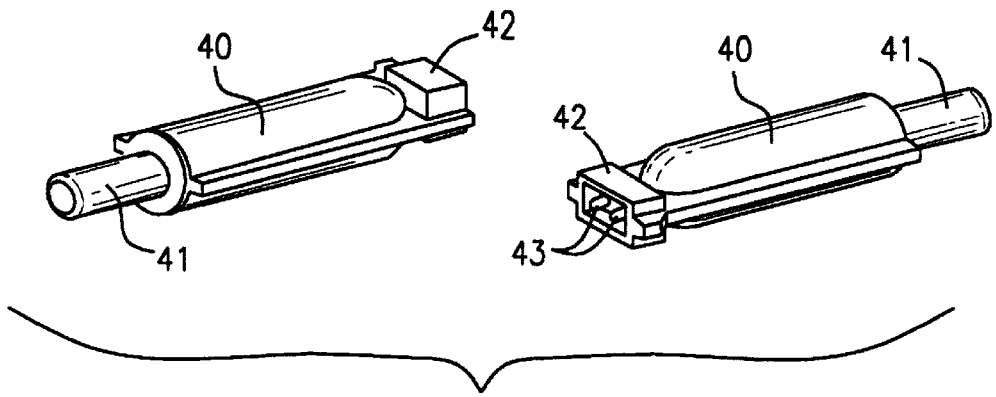

FIG. 5: Module from a medication unit and a gas generator

Figure 6:
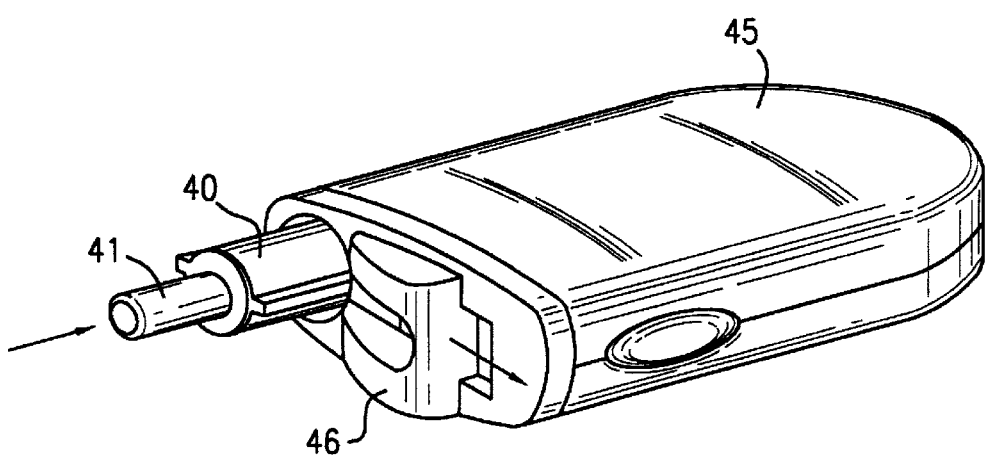
Figures 14, 14A:
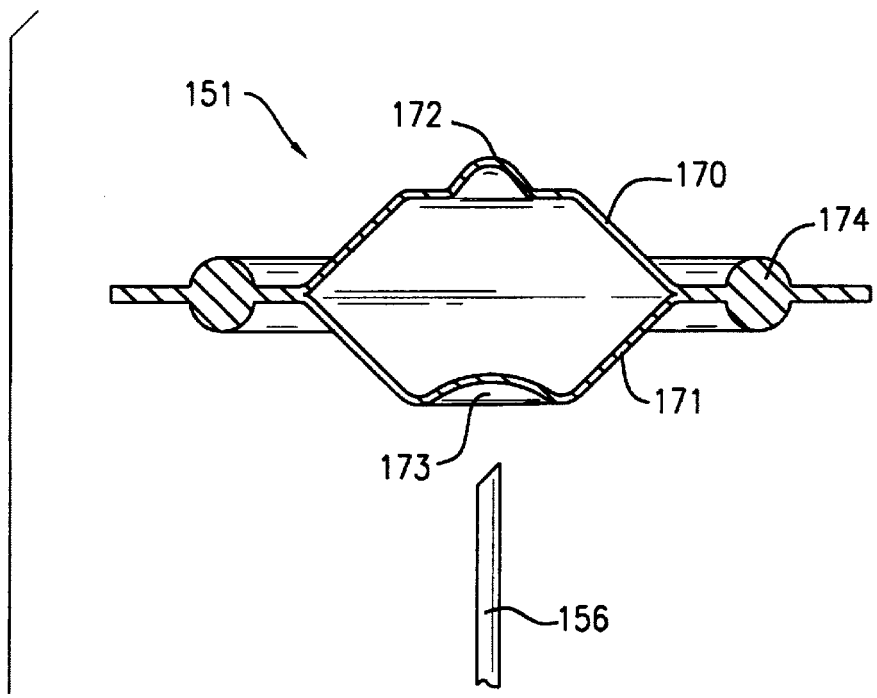
Figure 14B:
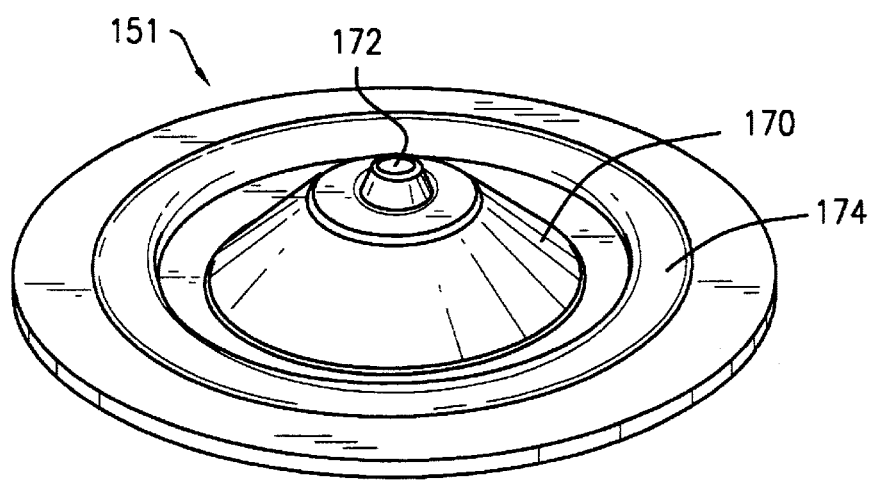

FIG. 6: Injection system in which a module according to FIG. 5 is inserted into a surrounding container FIG. 7: Injection system with adjustable free volume FIG. 7a: Improved adjustable free volume concept FIG. 8: Pressure curves for several free volumes FIG. 9: Injection kinetics for several free volumes FIG. 10: Injection system with gas leaks FIG. 11: Blow fill seal process under vacuum FIG. 12: Type A medication unit FIG. 13: Type B handling unit FIG. 14: Type B medication unit FIGS. 1 and 2 display a first embodiment of the injection system according to the invention prior to and after activation of the gas generator. In FIG. 1 a primary, squeezable container (1) can be recognized in which a liquid is located. The first container is surrounded by a surrounding container (2) in which the gas generator (5) is located in the form of an explosive material. Furthermore, a hollow space is located between the primary and the surrounding container which can be filled with gas or evacuated. Charging of this area with gas is advantageous when the rate of pressure increase in the surrounding container should be reduced whereas evacuation of the intermediate space is of advantage when a sharp pressure rise is desired. In most cases it is suitable to allow air at atmospheric pressure to fill the intermediate space during the production process. The first container (medication unit) possesses a channel at its frontal end which leads to an exiting orifice (4). The channel is located in the region in which the second region of the first container is located. In this region the first container is preferably relatively strongly built, to make possible a safe and in particular, a gas tight mounting. In its rear end (the first region) the container is fashioned in a squeezable manner. This first region is preferably fabricated from an elastic plastic like for example polyethylene or polypropylene. The first container is fabricated in an analogous fashion to disposable bottles for eye drops. Similarly they also have a region which can be squeezed by the user for the discharging of eye drops and an exiting orifice which can be brought to the eye. Production of the first container of the invention is therefore known to those skilled in the art from the field of disposable ampules for eye drops.

Despite the high pressures acting on the flexible region of the first container, no special provisions have to be made to increase its mechanical stability. This is due to the fact that the developing pressure is distributed relatively evenly over the whole outer shell of the first container such that no shearing forces arise which would give rise to mechanical strain. As is illustrated in FIG. 1, it is of advantage when the first container is, where possible, completely filled with liquid. This is preferred because of the fact that on the one hand, a pressure decrease due to the compressability of gas in air bubbles can occur and on the other hand there is the danger that such gas may be injected into tissue. It has however been discovered that the second named danger is of little significance because the impulse which can be transferred by air is small because of its low density and therefore normally penetration of the skin surface does not occur.

In FIG. 1 a closure (6) is illustrated, which seals the exiting orifice (4) prior to use of the system. This closure can be advantageously connected to the second region of the medication unit via a predetermined breaking point such that the removal of the closure can occur by breaking off (as illustrated) or by rotating (twisting). Such closures are also known from disposable ampules for eye drops. Such containers are preferably injection moulded as open containers into which liquid is filled. The closure is subsequently welded or melted in such a manner that a twisting of the projecting material part is possible. In this invention it is of advantage when the exiting orifice has contours and in particular the shape of the exiting channel is predetermined and is not influenced by the twisting such as is the case for ampules for eye drops. In the case of ampules for eye drops the twisting off of the closure creates the exiting channel so that the shape and the inner diameter of the exiting orifice is dependent on the twisting/rotating procedure. In preferred containers according to the invention, the exiting channel and the exiting orifice is in contrast already formed during the production process (which is usually an injection moulding process) and the predetermined breaking point, which mounts the closure to the container, is located outside the direct vicinity of the exiting orifice such that during the twisting no deformation of the exiting orifice occurs. A particular advantage of the device shown in FIG. 1 is that orifice diameters below 130 or better below 100 $\mu$m can be employed. Such small orifices decrease the pain during injection.

In FIG. 1, it is furthermore recognizable how the medication unit (1) and surrounding container (2) are connected to each other. In the case illustrated, a sealing material (13) is located between the containers which envelopes the second region of the medication unit (1) and seals the surrounding container from its surroundings. The arrangement of the first and second container is located in a stabilizing shell (7) which surrounds the surrounding container and which is closed using a screw cap (8). The screw cap serves furthermore to secure the seal (13). However, other types of closures and other mechanisms to fix the closure on the second container can be employed.

FIG. 1 shows a disposable module which comprises the medication unit (1) and the surrounding container (2) in which the gas generator (5) is located. For repeated injections the user only has to replace a used diposable module by an unused one.

It can be recognized from FIG. 2, how the first flexible region of the medication unit is compressed by the gas liberated in the surrounding container (10) and expels a jet of liquid (12). Furthermore, in FIGS. 1 and 2 a device for the activation of the gas generator (5) is illustrated which exhibits electrical contacts (9) leading from the surrounding container to the outside, between which a hot wire is located on the inside of the surrounding container. When an electrical current flows through the hot wire, the hot wire heats up to such a temperature that the explosive substance which serves as a gas generator (5) ignites.

To perform an injection procedure with an injection system according to the invention, the device illustrated in FIG. 1 and FIG. 2 including the exiting orifice is placed on the skin and the gas generator then activated.

A second embodiment of the injection system of the invention is illustrated in FIGS. 3 and 4. These figures show a disposable module which comprises a medication unit, a surrounding vessel and a gas generator.

Between the reservoir (20) and the explosion chamber (21), a primary membrane (23) is located, which by activation of the gas generator is locomoted from the position illustrated in FIG. 3 to the position illustrated in FIG. 4. The membrane (23) can be fabricated from a plastic such as polyethylene or also from a metal foil such as aluminum. In this embodiment of the injection system according to the invention, components which can be slid against each other and the associated sealing problems are avoided. In FIGS. 3 and 4 moreover, a secondary membrane is illustrated which can be employed to advantage. After activation of the gas generator, the first membrane (23) is moved in the direction of the nozzle (25) and compresses the liquid contained in the first container (20), whereby the secondary membrane (24) is forced in the direction of the nozzle (25) and whereby it is pierced by a hollow needle (33) which points in the direction of the first container. After piercing of the secondary membrane the liquid located in the first container is forced through the nozzle. FIGS. 3 and 4 furthermore show an air vent (31) which allows air to escape from the space (32) when the secondary membrane (24) is forced against the hollow needle (33). The air vent (31) comprises an annular space around the hollow needle which is connected to bores in a second molded part (27) and clasp (28). The air vent (31) avoids that a pressure is build up in the space (32) when the secondary membrane is moved. The air vent (31) is advantageous to improve the seal between secondary membrane (24) and hollow needle (33) after piercing. The embodiment illustrated in FIGS. 3 and 4 has a first and a second shell (26,27) which are held together by a clasp (28). The primary and secondary membranes are clamped between the shells. The first preformed part (26) has a recess in which a shell (29) made from an electrically insulating material (29) is located which is penetrated by an electrical contact (30). The first shell (26) is fabricated preferably from an electrically conducting material such that the application of an electrical potential between first shell (26) and the electrical contact (30) gives rise to the ignition of an explosive substance contained in the explosion chamber (21). If the explosive substance is suitably selected, the hot wire or the like can be disposed of. Such explosive substances usually contain a finely divided metal such as for example aluminum by virtue of which a certain electrical conductivity of the explosive substance is achieved.

FIG. 5 illustrates a disposable unit for an injection system in which the medication unit and the second container are separated from each other. In FIG. 5 an embodiment of a medication unit (40) is illustrated whose exiting orifice is closed by a knob (41). Furthermore, a gas generator (42) is illustrated in the form of an explosive substance which is located outside but connected to the medication unit (40). In the rear view of the module illustrated too, electrical contacts (43) are recognizable with which the gas generator (42) can be ignited. The medication unit of FIG. 5 has an unique topology in which the gas generator is connected to but outside the medication unit. This type of medication unit minimizes the amount of material which is needed to produce the medication unit. This arrangement can be manufactured in a blow fill seal process which is described further below or an injection molding process. With both processes the medication unit can be formed having the gas generator attached thereto. The connecting piece of material can be formed from the same material as used for medication unit and material enclosing the gas generator. This further simplifies the manufacturing process of the handling unit shown in FIG. 5.

In FIG. 6 a handling unit is illustrated in which the module illustrated in FIG. 5 can be inserted. For this purpose, the handling unit (45) possesses a hollow space on its inside in which the module illustrated in FIG. 5 can be inserted. For this purpose, the slide (46) is pushed first of all to the side so that the hollow space in the handling unit is opened. The module, in accordance with FIG. 5, is inserted and the slide closed which results in a sealing of the first container against the second container. The handling unit has electrical contacts on its inside which can be connected to electrical contacts (43) of the module and via which using a battery ignition can take place. After use, the spent first container from the handling unit (45) can be withdrawn by opening the slide (46) and if necessary be replaced by a new module.

Figure 7:
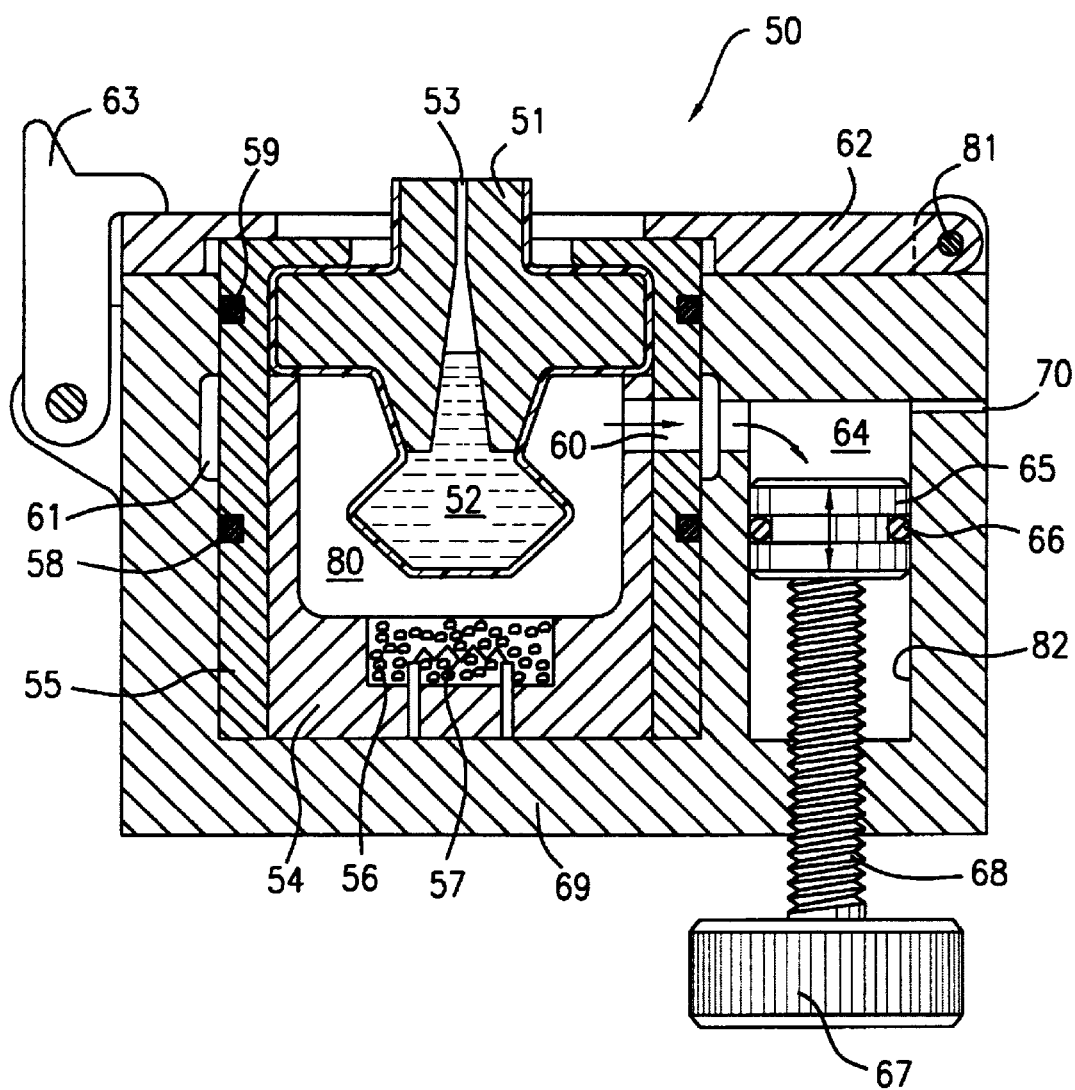

FIG. 7 shows an injection system (50) with an adjustable free volume to regulate the pressure of the liquid injection jet. Within this system there is shown a medication unit (51) which will be described in more detail in the following. This medication unit (51) has a reservoir for liquid medication (52) and a nozzle (53) for expelling a liquid jet of medication. The embodiment shown in FIG. 7 primarily serves to explain the adjustable free volume concept and is not limited to a specific type of medication unit. The medication unit (51) is seated on an inner shell (54) which is made from a material that can withstand pressures generated within the explosion chamber (80). Suitable materials for this inner shell are hard plastics as for example polymethylmetacrylat and polycarbonates. The inner shell (54) also can be made from metals as steel or brass. The inner shell (54) can also be made from flexible materials as polyethylene or polypropylene if the medication unit is surrounded by a rigid receptable during ignition of the explosive. The inner shell is surrounded by an outer shell (55). The outer shell (55) can be made from the same materials as the inner shell. The two shells serve to hold the medication unit in between so that an explosion chamber (80) is formed in which at least the reservoir is being disposed. Within the inner shell there is also located an explosive or propellant (56) which can be ignited by a heatwire (57) or the like. FIG. 7 does not show any electrical contacts within the device body (69) for connecting electrical energy to the heatwire (57) since this was already described previously and it is also known in the prior art to make such contacts. FIG. 7 discloses a disposable module which is formed by the medication unit (51), the shells (54,55) and the gas generator (57).

The outer shell (55) shown in FIG. 7 has two O-ring seals (58, 59) which seal the outer shell against the device body (69). Optionally the system shown in FIG. 7 has a gas groove (61) disposed in the device body (69) and surrounding the outer shell annularly. In a preferred embodiment the medication unit has a tubular shape and the device body (69) has a tubular recess for receiving the medication unit. Hence an user of the injection system can place the medication unit into the recess in any rotational orientation. The medication unit shown has one gas port (60) with a cross section of 2 to 5 mm. Typically the gas port (60) has the shape of a cylindrical bore it is also possible to employ medication units with two or more gas parts which are typically arranged on a circle in a common distance from the bottom of the medication unit. The gas groove (61) guarantees that there is a free passage from the explosion chamber (80) to the free volume (64) regardless of the rotational orientation of the medication unit within the device body (69). Analogously there is an embodiment possible where the gas groove (61) is realized as a groove in the outer circumference of the medication unit. In such an embodiment there is no need for an gas groove in the device body (69) since the groove in the medication unit readily guarantees a free gas passage. FIG. 7 also shows how the injection unit is held within the device body (69). The injection unit is disposed within a recess in the device body (69) and a cover (62) is closed above the injection unit. The cover (62) comprises a recess through which the nozzle (53) of the medication unit (51) projects. The cover (62) is held within the closed position by a latch (63). For removal of the injection unit the latch is opened and the cover is rotated around the hinge (81). The injection unit now can be taken out of the device body (69).

An important aspect of the embodiment shown in FIG. 7 is the gas port (60) which connects the explosion chamber (80) with an adjustable free volume (64). The gas port (60) traverses both inner and outer shell. Within the present invention there are also embodiments contemplated which have nor or only one shell holding the medication unit (51). In those embodiments the gas port (60) would traverse no shell or the one shell present. Advantageously the gas port can be provided with a filter means as explained below for FIG. 7a.

FIG. 7 further shows an adjustable free volume (64) into which gases from the explosion chamber (80) can expand. The free volume (64) can be adjusted by moving a piston (65) within a free volume chamber by rotation of a knob (67). The knob (67) is attached to a screw (68) which rotates in a nut of the device body (69). With regard to the high pressures within the free volume (64) the piston and screw have to be made from stable materials such as a metal. To avoid a leakage of gas from the adjustable free volume (64) into the remaining chamber the piston (65) should be sealed against the cylinder (82). It is advantageous if the free volume (64) can be varied between zero and a volume four times the volume of the explosion chamber (80). In particular it is advantageous if the free volume (64) can be varied between zero and a volume two times the volume of the explosion chamber.

FIG. 7 further shows a vent (70) allowing gases to escape slowly from the adjustable free volume (64). The vent (70) should be dimensioned that the pressure in the first milliseconds after ignition is only diminished little by gas escaping through the vent. On the other side the vent has to assure that the pressure within the injection systems is equilibrated with the environmental pressure when the user opens the device. Particularly well suited vent diameters have been found in the range of 0.01 to 0.5 mm.

Figure 7A:
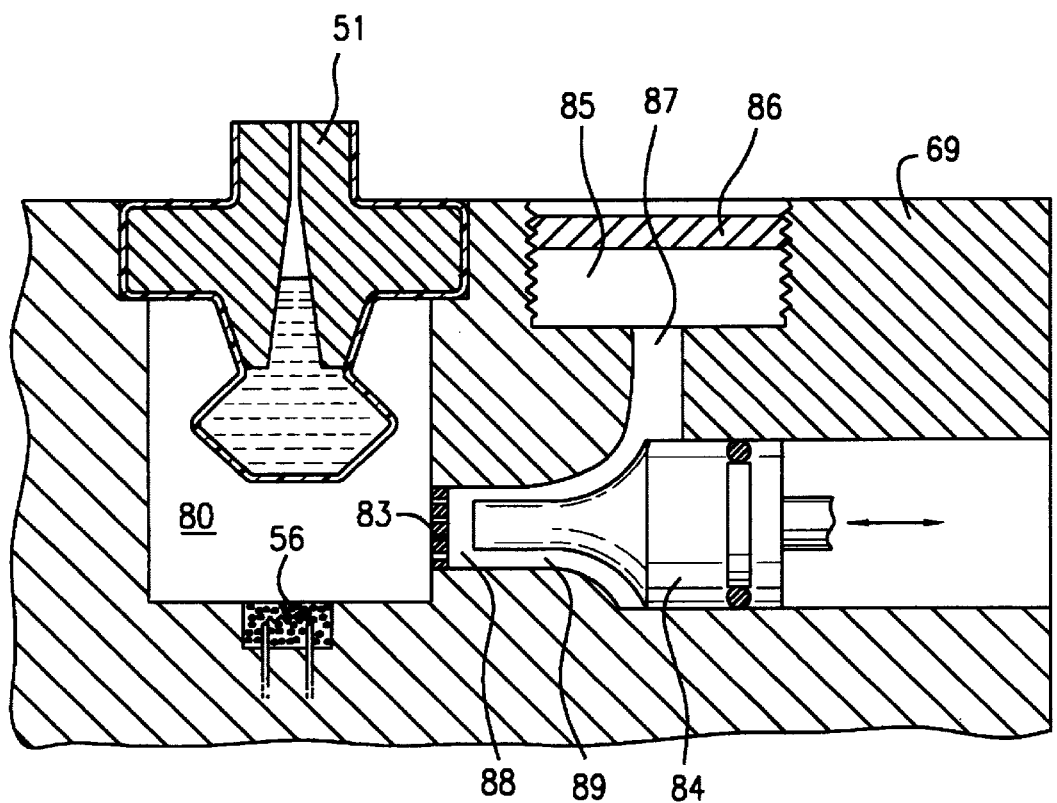

FIG. 7a shows an improvement of the adjustable free volume concept. Explosion chamber (80) and medication unit (51) are only shown schematically. In FIG. 7a there is depicted a filter means (83). The filter means (83) is disposed between the explosion chamber (80) and the adjustable free volume. The filter means (83) has holes of approx 0.5 to 1 mm in diameter. Dependent on the particular needs there can be two to ten of said holes. The total free diameter of all holes should provide a flow area equivalent to a single hole in the range of 2 to 8 mm. The filter means has two functions. At first the filter means prevents larger particles of the explosive from escaping the explosion chamber. This keeps the adjustable free volume clean and ensures that the total amount of the explosive in combusted. The latter is very important to make the explosion process reproducible so that the pressure curves are predictible. If particles of more than 1 mm would escape the explosion chamber these particles would not burn down completely resulting in a loss of gas to be produced by the explosion process. The other function of the filter means (83) is a flow resistance for the gas escaping the explosion chamber.

The filter means can be made from materials as steel, hard alloys and ceramics. It is even possible to produce the device body (69) with a wall remaining between explosion chamber and adjustable free volume, said wall being provided with holes later on. It is further preferred to employ filter means which are porous and have holes in the desired range.

FIG. 7a further shows an adjustable free volume (88) which is adjusted not only by a planar piston as shown in FIG. 7 but with a tapered piston (84) and a correspondingly shaped recess (89). The gas from the explosion chamber (80) has to pass the recess (89). With such a tapered piston (84) and a corresponding recess (89) it is possible to vary small volumes of the adjusted volume smoothly. And further it is possible to provide a non-linear volume increase over a linear travel distance of the piston (84). This can be of importance to provide an easy adjustment facility for penetration depth and/or skin type. The tapered portion of the piston can have spherical, paraboloid or inverse-paraboloid shape as shown in FIG. 7a. A further improvement which FIG. 7a shows is the combination of two free volumes (88, 85). The first free volume (88) can be adjusted by the piston (84). The second free volume (85) can be fixed or adjustable by a second piston (86). First and second free volume are connected to each other by a channel (87). The second free volume (85) should enable adjustment of the largest pan of the total free volume. This adjustment normally is done by the manufacturer. The fine adjustment of the total free volume is done by the user via the piston (84) in the way as described with reference to FIG. 7. It is preferred to employ a piston which has a tapered portion as described above as well as a cylindrical portion. The location of the channel (87) can be chosen so that the channel is closed by the cylindrical portion when the adjustable free volume is minimal and said channel being opened continuously when the adjustable free volume (88) is increased. This arrangement provides a good control of the pressure curve since not only the free volume can be adjusted but also the speed of filling this volume can be controlled by virtue of the adjustable flow resistance.

Figure 8:
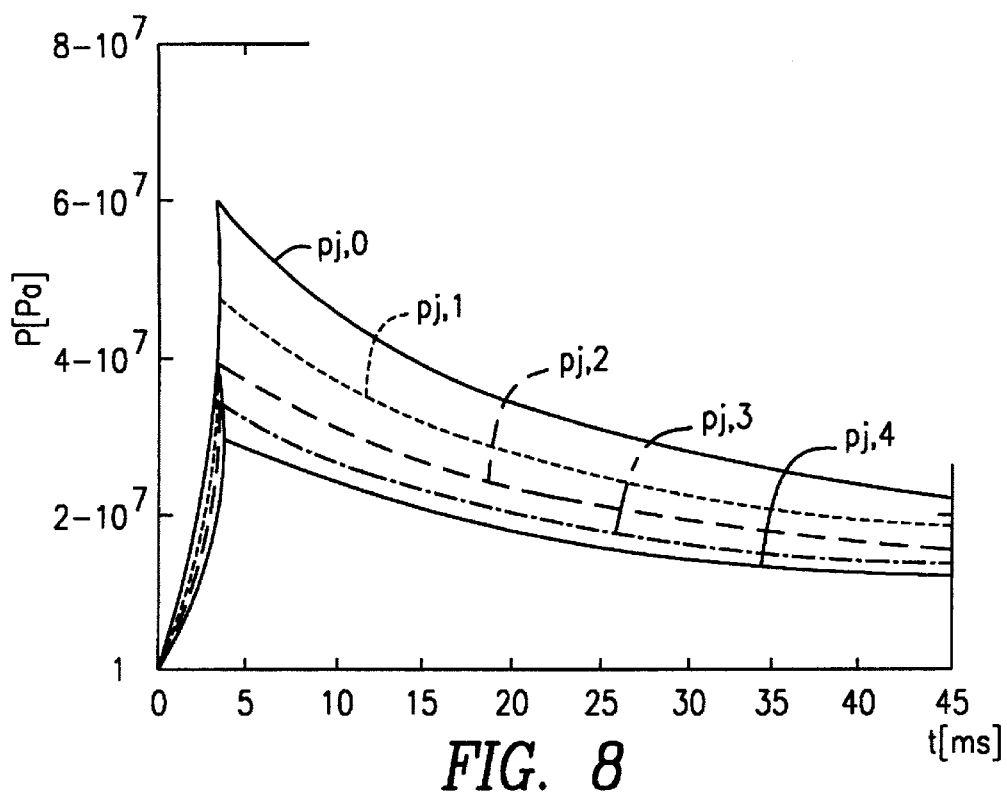

FIG. 8 shows a pressure over time diagram for several free volumes. The figures were generated by using a device as shown in FIG. 7 with an explosion chamber (80) of 1 cm$^3$ and a volume of explosive of 0.7 cm$^3$. The explosive used for these experiments was nitrocellulose. FIG. 8 shows on the ordinate the pressure within the explosion chamber (80) in pascal and the time is shown on the abscissa in milliseconds. The highest pressure within the explosion chamber is obtained with a zero free volume (see curve designated $p_j,0$). The other curves were obtained with a free volume (64) of 0,5 ccm ($p_j,1$); 1,0 cm$^3$ ($pj_2$); 1,5 cm$^3$ ($pj_3$) and 2,0 cm$^3$ ($pj_4$). The figures show that the pressure curve for injection can be easily controlled by using an adjustable free volume.

Figure 9:
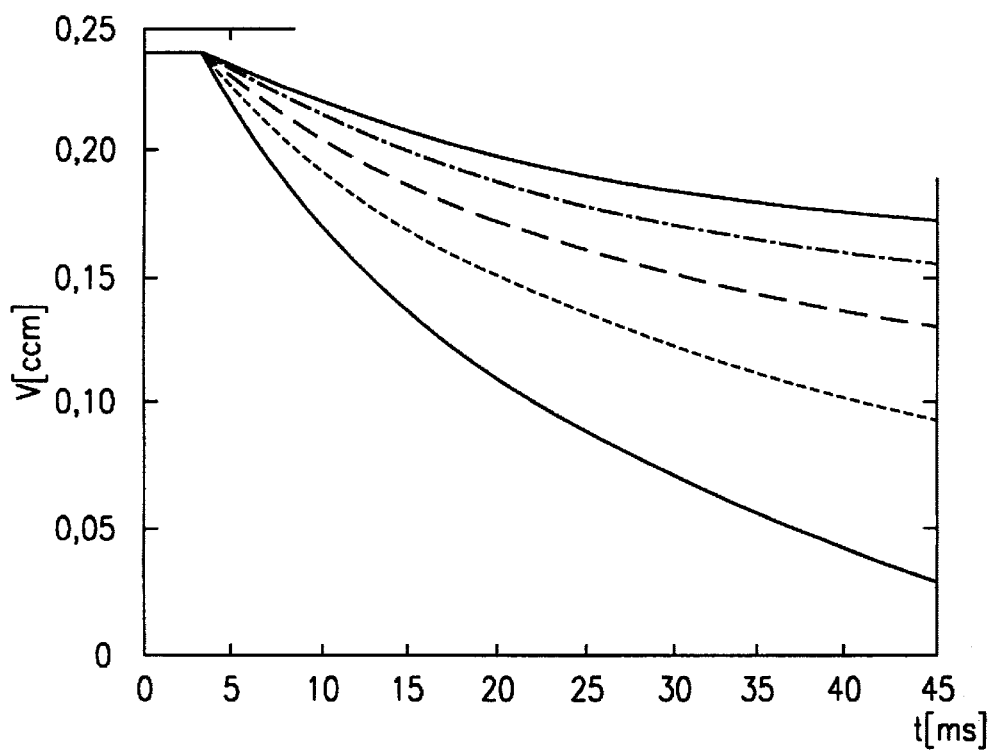

FIG. 9 shows how fast the liquid medication is being expelled from the reservoir using the before mentioned free volumes. On the ordinate there is given the remaining volume in the reservoir and on the abscissa there is given the time in milliseconds. Within these experiments there was used an initial liquid volume of 0,24 ccm. The figure shows that with a zero free volume (lowermost curve) the volume is nearly totally expelled within 45 ms. With a free volume of 2,0 ccm (uppermost curve) it is possible to slow down the rate of expulsion significantly. The other curves shown in FIG. 9 belong to 1,5 ccm, 1,0 ccm and 0,5 ccm free volume from top to bottom.

Figure 10:
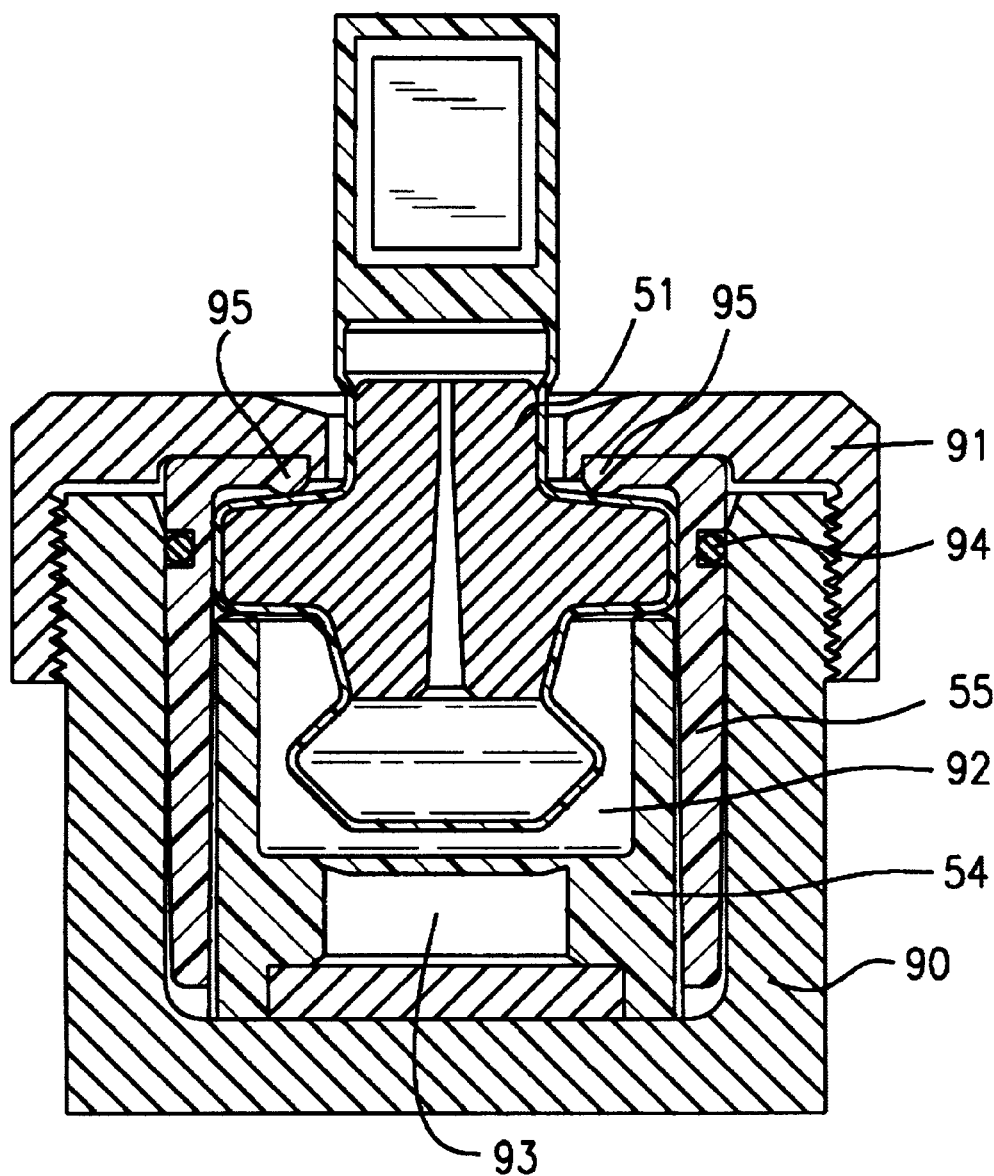

FIG. 10 shows a further system comprising an injection unit and a unit for holding said injection unit. The injection unit comprises a medication unit (51) which is held by arrangement of an inner shell (54) and an outer shell (55). The injection unit is placed in a device body (90) and is secured within said device body by a cover (91) which is screwed onto the device body. The arrangement shown in FIG. 10 does not have an adjustable free volume to control the pressure of the injection. Instead the device of FIG. 10 uses a venting concept to vent air from the explosion chamber (92). After the explosive (93) has been ignited the gas pressure can escape the explosion chamber (92) by a leak between the medication unit (51) and the inner shell (54). The gas then finds a way through the space between inner and outer shell and then between the outer shell and the device body (90). An O ring seal (94) prevents flow of gas through a gap between outer shell (55) and device body (90). A further way the gas can take from explosion chamber (92) is through a leak between the inner shell (54) and the medication unit (51) then passing a gap between medication unit and outer shell and finally leaving the system in a controlled way through a weak sealing (95) between medication unit (51) and outer shell. By adapting the flow resistance of the system for the combustion gases the pressure over time curve can be adapted to provide proper injections.

The embodiment shown in FIG. 10 is particularly well suited to provide single shot injection systems which can be disposed completely after use. The disposable module does not only comprise medication unit, surrounding chamber and gas generator but also a stabilizing shell which gives mechanical stability to the surrounding chamber after ignition. It is possible to integrate an activator for the gas generator into this unit so that the user is provided with a stand alone injection system.

FIG. 12 shows a a longitudinal cut through a novel type of medication unit (120) for hypodermic injections. The liquid medication (121) is enclosed in a squeezable container (122) (volume shown: 0.2 cm$^3$). The container wall envelopes the medication as well as a nozzle unit (123). The nozzle unit is a specific embodiment of the second region of the medication unit, whereas the squeezable part below the nozzle unit is a specific embodiment of the first region. The medication unit has rotational symmetry in its lower region (squeezable container and nozzle unit) which simplifies insertion into a handling unit.

The shape of the squeezable container (122) is particularly useful. The squeezable container has a planar bottom part (126) connected by a widening wall part (127) to a tapering wall part (128). When pressure is applied to these wall parts (126,127,128) the container squeezes and the liquid medication is ejected through the nozzle unit (123). The specific shape of the squeezable container ensures a total ejection of the medication which is desirable to enable a precise dosing of medication to a patient. However, the shape shown in FIG. 12 is only for exemplary reasons and not to limit the claimed invention. The squeezable container is preferably made from polyethylene, polypropylene or PVC due to their flexible characteristics and their inert nature against common medication fluids. It is worth saying that it is a particular improvement over the prior art to employ even for the nozzle materials which do not affect nearly every medication. Furthermore, the medication is totally enveloped by sterile materials and can be opened in a way that no contamination of the fluid occurs.

FIG. 12 further shows the nozzle unit (123) having a channel (124) communicating with the squeezable container (122) at its first end and leading into a nozzle (125) at its second end. The outer shape of the nozzle unit is adapted to securely hold the medication unit within a handling unit. The nozzle unit has an inner region principally in form of a cylinder through which the channel runs and an integral ring part surrounding the inner part. It is of particular advantage that the enveloping wall (131) forming the squeezable container extends over the nozzle unit and envelopes the nozzle unit completely. This will become more clear when the production process of the medication unit is described below. It is particularly preferred to employ the same materials for nozzle unit and enveloping wall because in this case the two items are melting together at least partially which leads to a fluid tight connection. The melting process is normally achieved by the cold flow behaviour of these materials. The medication unit (120) is closed by a tab (130) which is connected to the enveloping wall (131) via a predetermined breaking region (132). Alternatively the tab (130) can be directly connected to the nozzle part (123) over a predetermined breaking region. FIG. 12 further shows an optional thin plate (129) overlaying the nozzle outlet. This plate is withdrawn when the tab (130) is removed from the medication unit. The thin plate can be a foil or the like which avoids the leakage of medication from the medication container. This effect can also be achieved by a thin integral wall closing the outlet end of the nozzle. However, the thin plate or the thin integral wall are only optional. It has shown that the leakage is only small or lacks totally when nozzle sizes employed in the present invention are used.

FIGS. 12 B and 12 C show perspective drawings of the medication unit (120). It can be seen from these figures that the region of the squeezable container and the nozzle unit have rotational symmetry whereas the tab (130) is generally planar to facilitate handling.

A nozzle to be employed in a medication unit for hypodermic injections preferably has an inner contour of rotational symmetry and an exponential slope. An exponential slope can reduce the radial velocity gradient of the liquid within the nozzle significantly. A nozzle of exponential slope is therefore of particular advantage when the medication contains substances which are sensible to shear forces. This is the case for molecules as nucleic acids, proteins etc. Preferred nozzle shapes are given by the following equation:

$$T = a \cdot \exp(b \cdot X)$$

wherein

X=x or $X = c + dx + ex^2 + fx^3$ with X as linear coordinate starting with X=0 at the nozzle outlet and r as radius of the nozzle a, b, c, d, e and f are coefficients to be chosen according to the particular conditions.

Coefficient a determines the diameter of the nozzle at the outlet and is an important factor determining the velocity of the ejected liquid. Preferably a is in the range of 0,04 to 0,08 mm. The other coefficients are dependend on the length of the nozzle, which in turn mostly depends on manufacturing requirements. It is particular preferred to have an exponential function with a turning point. Such a function therefore changes its direction of inflexion. The coefficient e can be zero, while it is preferred for the other coefficients to be unequal zero. A particular useful set of coefficients is:

c=−2,8615 d=0,7322 e=0,0
f=0,0038

When the exponential slope is problematic to produce, a polygon approximating an exponential slope can be employed.

A particular useful nozzle has three sections:

1st section: An inlet section a the end of the nozzle communicating with the liquid medication. The inlet section has a rounded shape so that a pressure change in this region is reduced as much as possible.

2nd section: A section of exponential slope as described above which is connected to the inlet section and the 3rd section continuously.

3rd section: Outlet section which terminates in the outlet surface from which the medication leaves the medication unit. In the region of the outlet the nozzle should not widen since this may lead to disintegrations of the liquid jet. In the outlet section a sharp edge between nozzle and outlet surface is therefore preferred.

As already mentioned plastics as PVC, polyethylene and polypropylene are preferred for the nozzle unit. Due to the high pressure during injection these soft materials deform significantly.

A first approach to comply with this problem is to employ a smaller nozzle as needed and let the nozzle widen during injection. Typical pressures during injection are in the range of 300–800 atmospheres. Provided a polyethylene nozzle with a diameter of 0,1 mm a pressure of 1000 bar would lead to a widening of approx. 50% of the original nozzle diameter.

A second approach is to surround the nozzle or at least the outlet section with a harder material. The nozzle can be surrounded by a metal ring, ceramics or a harder plastic as polymethylmethacrylate or the like. The surrounding materials does not contact the medication and therefore no disadvantageous interactions can occur. It has shown to be of particular usefulness to shrink the surrounding material onto the nozzle. However, if the nozzle has a thick wall made from a soft plastic the nozzle diameter may expand even if it is surrounded by a harder material. It is therefore advantageous to keep the nozzle wall below 1 mm. The surrounding material can be warmed to expand, put over the nozzle and cooled down to enclose the nozzle. Vice versa the nozzle can chilled and a ring of hard material put around the nozzle so that a tight fit is achieved during the warm up process of the nozzle. Other methods to apply a ring of hard material over the nozzle are press fitting or crimping.

The production of a medication unit as shown in FIG. 12 comprises the following steps:

a nozzle unit is formed, e.g. in an injection molding process an open ended container is formed (e.g. in a blow-fill-seal process)

liquid medication is introduced into the container the nozzle unit is introduced into the container through the open end the medication container is formed around the nozzle unit so that the wall encloses the nozzle unit and a predetermined breaking section and a tab are formed.

The before described medication unit of type A can be employed in a handling unit. Therefore the medication unit is placed in an explosion chamber so that the squeezable region (122) is located within the explosion chamber and the medication unit is hold with is ring part of the nozzle unit (131). Within the explosion chamber there can be deposited a gas generator. Such a handling unit provides the user with all disposable parts combined in one handling piece which is of particular advantage. The medication container of type A or a handling unit based thereupon can favourably be employed within an injection system with an adjustable free volume as described further below.

Type B medication unit and handling unit

FIG. 13 shows a type B handling unit (150) loaded with a corresponding type B medication unit (151). FIG. 13 A is a cross sectional planar view and FIG. 13 B a perspective drawing of a cutted handling unit.

In this embodiment the medication container (151) is sandwiched between a first shell (152) and a second shell (153) which are fixed together. Within the shown embodiment the second shell (153) has an extending portion closely surrounding the lower shell. However other fixations of the shells together are within the skill of an artisan in this field. The second shell further has a recess adapted to receive a medication unit. The first shell (152) contains an explosive (154) which can be ignited and then creates pressure within the explosion chamber (155). The embodiment shown in FIG. 13 does not have a wall to close the explosion chamber against the surrounding because this handling unit is designed to be placed in an injection system which provides a closing wall. However, handling units where a closing wall belonging to the handling unit shell is present are also in the scope of this invention. The second shell has a needle (156) inserted therein which serves as nozzle. The needle has a pointed tip at its first end facing into the handling unit to pierce the medication container. The second end of the needle points out of the upper shell so that it can be directed to a body surface where injection is desired. The handling unit further has a tab (157) connected to the second shell (153) via a predetermined breaking area (158). Within the tab (157) there is located a plate (159) overlaying the needle. This plate facilitates the production process of the handling unit.

An important aspect of the invention is the type B medication unit (151) which is shown in more detail in FIG. 14. FIG. 14 A shows a cross sectional view whereas FIG. 14 B is a perspective view. The medication unit (151) is made from a first segment (170) and a second segment (171) which are connected to one another so that a closed cavity for holding liquid medication therein is being formed. The two segments are preferably made from plastics. Particularly advantageous are polyethylene and polypropylene because of their inert behaviour against most types of medication. The segments can be produced by e.g. injection molding. The two segments can be glued, welded or melted together. Welding and melting are preferred because no glues are necessary which could adversly affect the medication. FIG. 14 shows a thickened portion (174) which annularly surrounds the medication cavity like a saturn ring. It has proven advantageous to use an additional amount of material in this region to ensure that the two segments can be readily welded together.

The second segment (171) has a concave portion (173) in the region where piercing of the medication unit occurs. The first segment (170) has a convex portion (172) which prevents piercing of this segment by the needle. For reasons of clarity FIG. 14 also shows the needle (156) located beneath the second segment (171) which is pierced. When pressure is generated in the explosion chamber (155) this pressure acts on the first segment (170) deforming this portion so that pressure is generated within the medication container. Due to this pressure the concave portion (173) of the second segment (171) flexes outwardly, contacts the needle (156) and is pierced. The pressure which is still acting on the first segment (170) deforms this segment until it closely lies on the inner wall of the second segment. However, the convex portion prevents piercing of the first segment. The convex portion can be covered by a membrane at its outer side which shelters the convex portion against combustion gases and pressure. A further aspect of type B handling unit is that the upper shell (153) has a recess which supports the first segment (170) so that this segment only deforms in the concave region.

LIST OF REFERENCE NUMERALS (1) first, squeezable container/medication unit
(2) surrounding container
(3) liquid
(4) exiting orifice
(5) gas generator
(6) closure
(7) stabilizing shell
(8) screw cap
(9) electrical contacts
(10) gas
(12) liquid jet
(13) sealing material
(20) reservoir
(21) explosion chamber
(23) primary membrane
(24) secondary membrane
(25) nozzle
(26) first shell
(27) second shell
(28) clasp
(29) electrically insulating material
(30) electrical contact
(31) vent
(32) space
(33) hollow needle
(40) medication unit
(41) closing knob/peg
(42) gas generator
(43) electrical contact
(45) handling unit
(46) slide
(50) injection system with adjustable free volume
(51) medication unit
(52) liquid medication
(53) nozzle
(54) inner shell
(55) outer shell
(56) propellant/gas generator
(57) heat wire
(58) seal
(59) seal
(60) gas port
(61) gas groove
(62) cover
(63) latch
(64) adjustable free volume
(65) piston
(66) seal
(67) knob
(68) screw
(69) device body
(70) vent
(80) explosion chamber
(81) hinge
(82) cylinder
(83) filter means
(84) tapered piston
(85) adjustable second free volume
(86) second piston
(87) channel
(88) adjustable first free volume
(89) recess
(90) device body
(91) cover
(92) explosion chamber
(101) medication container
(102) liquid medication
(103) headspace
(104) opening
(105) chamber
(106) seal
(107) vacuum stream
(108) vacuum
(109) channel
(110) heated pinching tools
(111) air tight closure
(120) type A medication unit
(121) liquid medication
(122) medication container/first squeezable region
(123) nozzle unit/second region
(124) channel
(125) nozzle
(126) bottom of medication container
(127) widening wall part
(128) tapering wall part
(129) plate overlaying nozzle outlet
(130) tab
(131) wall material
(132) predetermined breaking region
(150) type B handling unit
(151) type B medication unit
(152) first shell
(153) second shell
(154) explosive
(155) explosion chamber
(156) needle
(157) tab
(158) predetermined breaking region
(159) plate
(170) first segment
(171) second segment
(172) convex portion
(173) concave portion
(174) annular wall

What is claimed is:

1. A hypodermic injection system for injecting liquids, which comprises:

(a) a medication unit configured and dimensioned to store a volume of liquid to be injected, the medication unit having first region and a second region that are in liquid communication with each other, the first region being deformable and the second region having at least one orifice;

(b) an explosion chamber configured and dimensioned so that the medication unit is located at least partially within the explosion chamber and so that pressure generated within the explosion chamber would cause the first region of the medication unit to deform so as to reduce the volume within the medication unit, the explosion chamber further having a gas port for exhausting gas from the explosion chamber;

(c) an activatable gas generator located inside the explosion chamber, the gas generator being capable of generating a pressure within the explosion chamber when activated;

(d) an activation unit for activating the gas generator; and
(e) a free volume chamber having a variable volume, the free volume chamber being in fluid communication with the explosion chamber via the gas port.

2. The hypodermic injection system according to claim 1, wherein the free volume chamber is formed by a housing in which a piston is movably located, the position of the piston within the housing determining the volume of the free volume chamber.

3. The hypodermic injection system according to claim 1, therein the gas port has a cross-section in the range of 2 mm to 5 mm.

4. The hypodermic injection system according to claim 1, wherein the volume of the free volume chamber can be varied between a volume of zero and a volume of four times the volume of the explosion chamber.

5. The hypodermic injection system according to claim 1, wherein the free volume chamber has a vent.

6. The hypodermic injection system according to claim 5, wherein the vent has a cross-section of 0.01 mm to 0.5 mm.

7. The hypodermic injection system according to claim 1 further comprising a filter located between the explosion chamber and the free volume chamber, the filter being configured and dimensioned so as to filter gas exiting the explosion chamber and entering the free volume chamber.

8. The hypodermic injection system according to claim 7, wherein the filter has a plurality of holes, each with a diameter in the range of 0.5 mm to 1 mm.

9. The hypodermic injection system according to claim 8, wherein the total area of all the holes in the filter provides a flow area equivalent to a single hole having a diameter in the range of 2 mm to 8 mm.

10. The hypodermic injection system according to claim 1, wherein the free volume chamber is partitioned into a first free volume portion and a second free volume portion, the first free volume portion and the second free volume portion being connected by a channel.

11. The hypodermic injection system according to claim 10, wherein at least one of the first free volume portion and the second free volume portion has an adjustable volume.

12. The hypodermic injection system according to claim 11, wherein the first free volume portion is adjustable by a user and the second free volume portion is adjusted by the manufacturer.

13. The hypodermic injection system according to claim 1, wherein the free volume chamber is formed by a housing and a tapered piston that moves within the housing, the housing being configured and dimensioned to correspondingly conform to the piston when the volume of the free volume chamber is minimal.

14. The hypodermic injection system according to claim 13, wherein the housing of the free volume chamber has a first free volume portion, a second free volume portion, and a channel which connects the first free volume portion with the second free volume portion.

15. The hypodermic injection system according to claim 14, wherein the tapered piston has a tapered portion and a cylindrical portion, the channel being configured and dimensioned within the housing so that the channel is closed when the first free volume portion has a minimal volume and opened when the volume of the first free volume portion is increased.

16. A handling unit for use in a hypodermic injection system, which comprises:
(a) a first shell having an explosion chamber and an explosive therein;
(b) a second shell having a piercing needle disposed therein, the piercing needle having a piercing end;

(c) a medication unit having a concave portion, the medication unit being sandwiched between the first shell and the second shell, the concave portion being arranged adjacent to the piercing end of the needle so that when pressure is applied to the medication unit by an explosion in the first shell, the medication unit generates a flexing deformation of its concave portion that leads to the piercing needle piercing the medication unit.

17. The handling unit according to claim 16, wherein the medication unit comprises a convex portion opposite to the concave portion which prevents piercing of the convex portion when the medication unit is deformed under pressure.

18. The handling unit according to claim 16, wherein the second shell has a recess to receive the medication unit therein and to support the portion of the medication unit that is adjacent to the second shell while allowing deformation of the concave portion.

19. The handling unit according to claim 16, wherein a space is formed between the concave portion of the medication unit and the second shell, and the handling unit has a vent that allows gas to escape from the space when this concave portion is moved towards the second shell.

20. Handling unit for hypodermic injections comprising
a first shell providing an explosion chamber and an explosive therein,
a second shell with a piercing needle disposed therein
a medication unit having a concave portion and being sandwiched between first and second shell
wherein the concave portion is being arranged beneath a pointed end of said needle and pressure applied to the medication unit generates a flexing deformation of the concave portion thus leading to a piercing of the medication unit.

21. Handling unit according to claim 20, wherein the medication unit comprises a convex portion in its first segment which prevents piercing of the first segment when the medication unit is deformed under pressure.

22. Handling unit according to claim 20, wherein the second shell has a recess to receive a medication unit therein and supporting said second segment to prevent deformation of the second segment with exception of the concave portion.

23. Handling unit according to claim 20 with a space (32) generated by the concave portion of the medication unit and the second shell (27), wherein said handling unit comprises a vent (31) which allows gas to escape from said space when the concave portion is moved in direction towards the second shell.

24. Hypodermic injection system comprising
a medication unit (51) in which liquid to be injected is stored and which has a first and a second region, said first region being squeezable or flexible and said second region having at least one orifice,
an explosion chamber (92) in which the medication unit is located at least partially and a pressure generated within said explosion chamber is deforming said first region of the medication unit,
an activatable gas generator (93) located inside the explosion chamber (92) which generates a pressure within the explosion chamber when activated, wherein said explosion chamber has a vent which allows gas escaping the explosion chamber in a controlled way.

25. Hypodermic injection system according to claim 24, wherein the flow resistance of the system for combustion gases is adapted to provide a desired pressure over time curve which leads to proper injections.

26. A medication unit for use in a hypodermic injection system, which comprises:
(a) a first region which is deformable and configured and dimensioned to store a liquid to be injected;
(b) a second region having at least one orifice, the second region being in liquid communication with the first region, the first region and the second region being separate pieces that are enveloped within a common wall;
(c) liquid medication contained within the first region, the second region, or both the first region and the second region; and
(d) a closure for closing the at least one orifice.

27. The medication unit of claim 26, wherein the medication unit is made from polyvinyl chloride, polyethylene, polypropylene, or mixtures thereof.

28. The medication unit according to claim 26, wherein the closure is connected to the second region via a connection having a predetermined breaking point.

29. A medication unit for use in a transdermal injection system, which comprises:
(a) a first region which is deformable and formed by a wall;
(b) a second region which is formed from a piece of material separate from that of the first region, the second region having at least one orifice and being in liquid communication with the first region, the first region and the second region being enveloped within in the wall of the first region;
(c) liquid medication contained within the first region and the second region; and
(d) a closure for closing the at least one orifice.

30. The medication unit according to claim 29, wherein the wall is integrally connected to a tab via a predetermined breaking region.

31. The medication unit according to claim 29, wherein the first region has a substantially planar bottom and a tapered wall portion connected to the bottom via a widening wall portion.

32. The medication unit according to claim 29, wherein the second region comprises a nozzle of rotational symmetry and exponential slope.

33. The medication unit according to claim 32, wherein the second region is made from a soft plastic and at least a part of the nozzle is surrounded on the outside by a ring made from a hard material.

34. A medication unit for use in a hypodermic injection system, which comprises a first segment and a second segment, each configured and dimensioned to be fixed to one another to form a cavity for a liquid medication, the second segment configured to have a concave portion that flexes outwardly when pressure is applied to the first segment, the first segment and the second segment being welded together and the medication unit having a thickened portion annularly surrounding the cavity at the point where the first segment and the second segment are welded together.

35. The medication unit according to claim 34, wherein the first segment has a convex portion.

* * * * *